(12) United States Patent
Zhang

(10) Patent No.: US 9,057,054 B2
(45) Date of Patent: Jun. 16, 2015

(54) ANTIGEN-SPECIFIC LONG-TERM MEMORY T-CELLS

(75) Inventor: Yi Zhang, Wallingford, PA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 305 days.

(21) Appl. No.: 13/379,075

(22) PCT Filed: Jun. 22, 2010

(86) PCT No.: PCT/US2010/039417
§ 371 (c)(1),
(2), (4) Date: Jan. 30, 2012

(87) PCT Pub. No.: WO2010/151517
PCT Pub. Date: Dec. 29, 2010

(65) Prior Publication Data
US 2012/0114623 A1 May 10, 2012

Related U.S. Application Data

(60) Provisional application No. 61/220,276, filed on Jun. 25, 2009, provisional application No. 61/308,058, filed on Feb. 25, 2010.

(51) Int. Cl.
| | |
|---|---|
| *C12N 5/0783* | (2010.01) |
| *A61K 31/436* | (2006.01) |
| *A61K 38/20* | (2006.01) |
| *A61K 45/06* | (2006.01) |
| *A61K 35/12* | (2006.01) |
| *A61K 39/00* | (2006.01) |

(52) U.S. Cl.
CPC ............ *C12N 5/0636* (2013.01); *A61K 31/436* (2013.01); *A61K 35/12* (2013.01); *A61K 35/17* (2013.01); *A61K 38/2013* (2013.01); *A61K 38/2086* (2013.01); *A61K 45/06* (2013.01); *A61K 2039/5158* (2013.01); *A61K 2039/57* (2013.01); *C12N 2501/04* (2013.01)

(58) Field of Classification Search
None
See application file for complete search history.

(56) References Cited

U.S. PATENT DOCUMENTS

| | | | |
|---|---|---|---|
| 2002/0119121 A1* | 8/2002 | Vitiello et al. | 424/85.2 |
| 2006/0159667 A1* | 7/2006 | Fowler et al. | 424/93.7 |
| 2008/0207644 A1 | 8/2008 | Sonis et al. | |
| 2008/0255029 A1 | 10/2008 | Marks et al. | |
| 2009/0012105 A1 | 1/2009 | Lane et al. | |

FOREIGN PATENT DOCUMENTS

| | | |
|---|---|---|
| WO | WO 2007037544 | 4/2007 |
| WO | WO 2007106503 | 9/2007 |
| WO | WO 2008071974 | 6/2008 |
| WO | WO 2009045308 | 4/2009 |

OTHER PUBLICATIONS

Gattinoni et al. (Nat Med. Jul. 2009;15(7):808-13. doi: 10.1038/nm.1982. Epub Jun. 14, 2009).*
K. Yonezawa, Nash and Nutritional Therapy 2005, pp. 92-99.*
Slavik et al., J Immunol 2001;166;3201-3209.*
Furukawa et al., Blood, Feb. 15, 2001, vol. 97, No. 4, pp. 987-993.*
Sinclair et al. (Nat Immunol. May 2008 ; 9(5): 513-521).*
Gattinoni et al. (J Clin Invest. Jun. 2005;115(6):1 616-26).*
Araki et al, Nature, vol. 460, Jul. 2, 2009, pp. 108-112 and Supplemental Methods p. 1, and data pp. 1-10.*
Tollerud et al. Journal of Clinical Immunology, vol. 9, No. 3, 1989, pp. 214-222.*
Prince et al. (Cell Immunol. Dec. 1992;145(2):254-62).*
Jung et al. (Biology of Blood and Marrow Transplantation 12:905-918 (2006)).*
[No Authors Listed]. "Temsirolimus: CCI 779, CCI-779, cell cycle inhibitor-779," Drugs R D, 5(6):363-367, 2004.
Araki et al., "mTOR regulates memory CD8 T-cell differentiation," Nature, 460(7251): 108-112, 2009.
Beevers CS et al., "Curcumin inhibits the mammalian target of rapamycin-mediated signaling pathways in cancer cells," Int J Cancer, 119(4): 757-764, 2006.
Blazar et al., "Bone marrow transplantation and approaches to avoid graft-versus-host disease (GVHD)," Philos Trans RSoc Land Bioi Sci, 360:1747-1787,2005.
Busch et al., "Isolation of peripheral blood CD4(+) T cells using RosetteSep and MACS for studies of DNA turnover by deuterium labeling," J Immunol Methods, 286(1-2):97-109, 2004.
Chang et al., "Asymmetric T lymphocyte division in the initiation of adaptive immune responses," Science, 315: 1687-1691,2007.
Chapman et al., "Everolimus," Drugs, 64:861-872, 2004.
Chen et al., "Marked differences in human melanoma antigen-specific T cell responsiveness after vaccination using a functional microarray," PLoS Med, 2(10):e265, 2005.
Chen et al., "TSC-mTOR maintains quiescence and function of hematopoietic stem cells by repressing mitochondrial biogenesis and reactive oxygen species," J Exp Med, 205: 2397-2408, 2008.
Chiang et al., "Phosphorylation of mammalian target of rapamycin (mTOR) at Ser-2448 is mediated by p70S6 kinase," J Biol Chem, 280: 25485-25490, 2005.
Dutt et al., "Naive and memory T cells induce different types of graft-versus-host disease," J Immunol, 179: 6547-6554, 2007.
Fang et al., "Phosphatidic acid-mediated mitogenic activation of mTOR signaling," Science, 294: 1942-1945, 2001.

(Continued)

*Primary Examiner* — Zachary Skelding
(74) *Attorney, Agent, or Firm* — Casimir Jones S.C.

(57) ABSTRACT

The present invention provides compositions, methods, and systems for generating antigen-specific long-term memory T-cells using mTOR pathway inhibitors. The present invention provides compositions, systems, and methods for administering antigen-specific long-term memory T-cells to a subject (e.g., to a subject with cancer in adoptive transfer type of procedures).

11 Claims, 9 Drawing Sheets

(56) References Cited

OTHER PUBLICATIONS

Fearon et al., "Arrested differentiation, the self-renewing memory lymphocyte, and vaccination," Science, 293 (5528):248-250, 2001.
Fearon et al., "The rationale for the IL-2-independent generation of the self-renewing central memory CD8+ T cells," Immunol Rev, 211:104-118, 2006.
Ferrara et al., "The pathophysiology of acute graft-versus-host disease," Int J Hematol, 78(3):181-187, 2003.
Frias et al., "mSin1 is necessary for Akt/PKB phosphorylation, and its isoforms define three distinct mTORC2s," Current Biology, 16(18): 1865-1870, 2006.
Gingras et al., "Regulation of 4E-BP1 phosphorylation: a novel two-step mechanism," Genes & Development, 13:1422-1437, 1999.
Goker et al., "Acute graft-vs-host disease: pathobiology and management," Exp Hematol, 29:259-277, 2001.
Hay et al., "Upstream and downstream of mTOR," Genes Dev, 18(16): 1926-1945, 2004.
Hinrichs et al., "Il-2 and Il-21 confer opposing differentiation programs to CD8+ T cells for adoptive immunotherapy," Blood, 111: 5326-5333, 2008.
Hinrichs et al., "Programming CD8+ T cells for effective immunotherapy," Curr Opin Immunol, 18:363-370, 2006.
Ho et al., "The history and future of T-cell depletion as graft-versus-host disease prophylaxis for allogeneic hematopoietic stem cell transplantation," Blood, 98: 3192-3204, 2001.
Holz et al., "Identification of S6 kinase 1 as a novel mammalian target of rapamycin (mTOR)-phosphorylating kinase," J Biol Chem, 280: 26089-26093, 2005.
Huang et al., "Mechanisms of resistance to rapamycins," Drug Resistance Updates, 4:378-391, 2001.
Huang et al., "Rapamycins: mechanism of action and cellular resistance," Cancer Biol Ther, 2: 222-232, 2003.
International Search Report and Written Opinion for International Application PCT/US2010/039417 dated Mar. 18, 2011.
June CH., "Adoptive T cell therapy for cancer in the clinic," J. Clin Invest, 117:1466-1476,2007.
June CH., "Principles of adoptive T cell cancer therapy," J. Clin Invest, 117:1204-1212,2007.
Kaech et al., "Effector and memory T-cell differentiation: implications for vaccine development," Nat Rev Immunol, 2: 251-262,2002.
Kaech et al., "Molecular and functional profiling of memory CD8 T cell differentiation," Cell, 111: 837-851, 2002.
Kane et al., "The PI-3 kinase/Akt pathway and T cell activation: pleiotropic pathways downstream of PIP3," Immunol Rev, 192:7-20, 2003.
Kenerson et al., "Effects of rapamycin in the Eker rat model of tuberous sclerosis complex," Pediatr Res, 57: 67-75, 2005.
Kim et al., "GbetaL, a positive regulator of the rapamycin-sensitive pathway required for the nutrient-sensitive interaction between raptor and mTOR," Molecular Cell, 11: 895-904, 2003.
Kim et al., "mTOR interacts with raptor to form a nutrient-sensitive complex that signals to the cell growth machinery," Cell, 110: 163-175,2002.
Lanzavecchia et al., "Understanding the generation and function of memory T cell subsets," Curr Opin Immunol, 17: 326-332, 2005.
Lanzavecchia et al., "Progressive differentiation and selection of the fittest in the immune response," Nat Rev Immunol, 2(12):982-987, 2002.
Lefrancois et al., "The descent of memory T-cell subsets," Nat Rev Immunol, 6(8):618-23, 2006.
Luckey et al., "Memory T and memory B cells share a transcriptional program of self-renewal with long-term hematopoietic stem cells," Proc Natl Acad Sci U S A, 103(9):3304-3309, 2006.
Masopust et al., "The role of programming in memory T-cell development," Curr Opin Immunol, 16(2):217-25, 2004.
McMahon et al., "Farnesylthiosalicylic acid inhibits mammalian target of rapamycin (mTOR) activity both in cells and in vitro by promoting dissociation of the mTOR-raptor complex," Molecular Endocrinology, 19(1):175-183, 2005.
Mothe-Satney et al., "Mammalian target of rapamycin-dependent phosphorylation of PHAS-I in four (S/T)P sites detected by phospho-specific antibodies," J Biol Chem, 275:33836-33843,2000.
Pause et al., "Insulin-dependent stimulation of protein synthesis by phosphorylation of a regulator of 5-cap function," Nature, 371: 762-767, 1994.
Peterson et al., "Translation control: connecting mitogens and the ribosome," Curr Biol, 8:R248-250, 1998.
Pullen et al., "Phosphorylation and activation of p70s6k by PDK1," Science, 279: 707-710, 1998.
Pullen et al., "The modular phosphorylation and activation of p70s6k," FEBS Letters, 410: 78-82, 1997.
Reiner et al., "Division of labor with a workforce of one: challenges in specifying effector and memory T cell fate," Science, 317(5838):622-625, 2007.
Reya et al., "Wnt signalling in stem cells and cancer," Nature, 434: 843-850, 2005.
Rosenberg, "Shedding light on immunotherapy for cancer," N Engl J Med, 350: 1361-1463,2004.
Saitoh et al., "Regulation of an activated S6 kinase 1 variant reveals a novel mammalian target of rapamycin phosphorylation site," J Biol Chem, 277: 20104-20112, 2002.
Sallusto et al., "Two subsets of memory T lymphocytes with distinct homing potentials and effector functions," Nature, 401:708-712,1999.
Sarbassov et al., "Prolonged rapamycin treatment inhibits mTORC2 assembly and Akt/PKB," Molecular Cell, 22(2): 159-168, 2006.
Sarbassov et al., "Redox regulation of the nutrient-sensitive raptor-mTOR pathway and complex," J Biol Chem, 280 (47): 39505-39509,2005.
Sarbassov et al., "Rictor, a novel binding partner of mTOR, defines a rapamycin-insensitive and raptor-independent pathway that regulates the cytoskeleton," Curr Biol, 14: 1296-1302, 2004.
Sarbassov et al., "Phosphorylation and regulation of Akt/PKB by the rictor-mTOR complex," Science, 307 (5712):1098-1101, 2005.
Sato et al., "Maintenance of pluripotency in human and mouse embryonic stem cells through activation of Wnt signaling by a pharmacological GSK-3-specific inhibitor," Nat Med, 10: 55-63, 2004.
Stephens et al., "Protein kinase B kinases that mediate phosphatidylinositol 3,4,5-trisphosphate-dependent activation of protein kinase B," Science, 279(5351):710-714, 1998.
Tokunaga et al., "mTOR integrates amino acid- and energy-sensing pathways," Biochem Biophys Res Commun, 313(2):443-446, 2004.
Trowbridge et al., "Glycogen synthase kinase-3 is an in vivo regulator of hematopoietic stem cell repopulation," Nat Med, 12(1):89-98, 2006.
Wherry et al., "Lineage relationship and protective immunity of memory C08 T cell subsets," Nat Immunol, 4: 225-234, 2003.
Wherry et al., "Molecular signature of C08+ T cell exhaustion during chronic viral infection," Nat Immunol, 27: 670-684, 2007.
Wu et al., "Induction of tumor immunity following allogeneic stem cell transplantation," Adv Immunol, 90:133-173, 2006.
Wullschleger et al., "TOR signaling in growth and metabolism," Cell, 124(3): 471-484,2006.
Yamashita et al., "Severe chronic graft-versus-host disease is characterized by a preponderance of C04(+) effector memory cells relative to central memory cells," Blood, 103: 3986-3988, 2004.
Zeng et al., "Synergy of IL-21 and IL-15 in regulating C08+ T cell expansion and function," J Exp Med, 201: 139-148, 2005.
Zhang et al., "Host-reactive C08+ memory stem cells in graft-versus-host disease," Nat Med, 11:1299-1305, 2005.
Zhang et al., "Alloreactive memory T cells are responsible for the persistence of graft-versus-host disease," J Immunol, 174: 3051-3058,2005.

\* cited by examiner

ANTIGEN-SPECIFIC LONG-TERM MEMORY T-CELLS

The present application claims priority to U.S. Provisional Applications 61/220,276 filed Jun. 25, 2009 and 61/308,058 filed Feb. 25, 2010, both of which are herein incorporated by reference in their entireties.

This invention was made with government support under Grant Nos. R01 CA102464, R01 AI47450, and P30CA46592 awarded by the National Institutes of Health. The government has certain rights in the invention.

FIELD OF THE INVENTION

The present invention relates to compositions, methods, and systems for generating antigen-specific long-term memory T-cells using mTOR pathway inhibitors. The present invention also relates to compositions, systems, and methods for administering antigen-specific long-term memory T-cells to a subject (e.g., to a subject with cancer in adoptive transfer type of procedures).

BACKGROUND

In the U.S. population, mortality associated with the 15 most common cancer types alone has been estimated to approach 170 deaths annually per 100,000 individuals. Currently, there are an estimated 1,437,180 new cases of cancer and 565,650 deaths each year. The economic burden of cancer has been estimated to exceed $96B in 1990 dollars.

Adoptive T cell immunotherapy has emerged as a novel cancer therapeutic approach, although its applications are not limited to cancer. Adoptive T cell immunotherapy has the potential to enhance anti-tumor immunity, augment vaccine efficacy and improve the therapeutic effects of chronic infections. There are general three goals for an effective adoptive T cell cancer immunotherapy. First, a sufficient number of potent tumor-reactive T cells must be present in the tumor-bearing host. Second, these tumor-reactive T cells have the capability to reach and infiltrate into the site of the cancer. Third, T cells in the tumor site have appropriate effector mechanisms to destroy cancer cells. Thus, development of novel approaches that augment the persistence, tumor-infiltration and killing activity of tumor-reactive T cells will lead to improving the efficacy of adoptive T cell cancer immunotherapy.

Current available technology to increase the frequency of tumor-reactive T cells from unprimed $CD8^+$ T cells are based on the following two methods: (1) stimulation with polyclonal activators (anti-CD3 and anti-CD28 specific antibodies) and (2) repeated stimulation with antigen-presenting cells loaded with specific antigens. The first method induces the expansion of whole T cell populations in a short time period (7 days or so) without selectively increasing the frequency of antigen-specific T cell clones. The second approach can selectively increase the frequency of antigen-specific T cell clones, but requires 6 weeks to generate sufficient numbers of tumor-reactive T cells for clinical application. Unfortunately, both methods induce the generation of tumor-reactive T cells that display transient cytolytic effects against tumor cells, but cannot persist long enough to destroy the tumor after adoptive transfer.

Thus, there exists an urgent need for improved methods for adoptive T cell immunotherapy, and particularly for methods resulting in generation and transfer of tumor-reactive T cells that are both cytolytic against target cells and that have the ability to persist in vivo for sufficiently long periods of time.

SUMMARY OF THE INVENTION

The present invention provides compositions, methods, and systems for generating antigen-specific long-term memory T-cells using mTOR pathway inhibitors. The present invention provides compositions, systems, and methods for administering antigen-specific long-term memory T-cells to a subject (e.g., to a subject with cancer in adoptive transfer type of procedures).

In particular embodiments, the present invention provides methods of generating antigen-specific memory T-cells comprising: contacting unprimed CD8+ T-cells with an antigen (or antigen-primed antigen presenting cells), at least one cytokine, antigen presenting cells, and an mTOR pathway inhibiting agent under conditions such that CD8+ memory T-cells specific to the antigen are generated. In other embodiments, the present invention provides methods of generating antigen-specific memory T-cells comprising; a) providing: i) an antigen (or antigen-primed antigen presenting cells), ii) antigen-presenting cells, iii) an mTOR pathway inhibiting agent (e.g., mTOR1 or mTOR2 pathway inhibiting agent), and iv) T-cells, wherein the T-cells are unprimed CD8+ T-cells; and b) contacting the T-cells with the antigen (or the antigen-primed antigen presenting cells), the at least one cytokine, the antigen presenting cells, and the mTOR pathway inhibiting agent under conditions such that CD8+ memory T-cells specific to the antigen are generated. In additional embodiments, the CD8+ memory T-cells have the ability to generate both effector and memory T cells upon secondary challenge of the antigen. In certain embodiments, the CD8+ memory T-cells are generated in vitro, while in other embodiments, they are generated in vivo. In particular embodiments, the mTOR pathway inhibiting agent inhibits mTOR function (e.g., mTOR activity, FRAP1/mTOR expression, mTOR protein level, mTOR stability). In other embodiments, the mTOR inhibiting agent is configured to reduce mTOR function (e.g., mTOR activity, FRAP1/mTOR expression, mTOR protein level, mTOR stability) and/or the function of other mTOR pathway members (e.g., IRS1, PI3K, PDK1, Akt, PKC, Rac, Rho, LKB1, Rheb, FKBP, mTOR, mLST8/GβL, S6K, S6, 4EBP1, rS6, eIF4E, eIF3, eIF4A, eIF4G, eIF4B, raptor, Vps34, rictor, PTEN, GSK3, LKB1, AMPK, RTP801/L, HIF1, REDD1, TSC1, TSC2) within the subject. In additional embodiments, the mTOR pathway inhibiting agent is rapamycin or a rapamycin derivative selected from the group consisting of CCI-779, everolimus (RAD-001), and AP23573.

In particular embodiments, the present invention provides methods of generating antigen-specific memory T-cells in vivo comprising: administering an antigen and an mTOR inhibiting agent to a subject under conditions such that CD8+ memory T-cells specific to the antigen are generated in the subject in an amount greater than the amount that would be generated with the antigen without the mTOR inhibiting agent. In further embodiments, the subject is further administered at least one cytokine (e.g., IL-2, IL-21, and/or IL-15, or mimetics thereof).

In certain embodiments, the T-cells are further contacted with at least one cytokine. In particular embodiments, the at least one cytokine comprises IL-2 (or IL-2 mimetic). In other embodiments, the at least one cytokine comprises IL-21 (or an IL-21 mimetic). In particular embodiments, the at least one cytokine is IL-2 and IL-21. In further embodiments, the CD8+ memory T-cells are $CD44^{lo}$ and $CD62L^{hi}$. In other embodiments, the CD8+ memory T-cells are $CD44^{hi}$ and $CD62L^{hi}$. In particular embodiments, the CD8+ memory T-cells are $CD62L^{hi}$. In other embodiments, the T-cells are isolated from a donor or eventual recipient (e.g., the unprimed T-cells are obtained from a subject and the resulting antigen-specific memory T-cells are administered back to the same subject). In particular embodiments, the T-cells are obtained from human peripheral blood. In some embodiments, the antigen-presenting cells are selected from the group consisting of bone marrow cells, peripheral blood cells, and mitogen-activated B lymphoblast cells. In further embodiments, the antigen presenting cells express high levels of CD86, CD40, and/or 4-1BBL. In further embodiments, the unprimed CD8+ T cells are IFN-γlo granzyme Blo CD44lo, CD62Lhi, CCR7hi, CD8+ T cells. In particular embodiments, the methods further comprise multiple rounds of the contacting the unprimed CD8+ T cells in the presence of antigen, antigen-presenting cells, and an mTOR-inhibiting agent.

In particular embodiments, the CD8+ memory T cell express elevated levels of at least one gene selected from the group consisting of: Ezh2, Hells, Bmi1, Survivin, p18Ink4c, and p21 (e.g., one of these genes, two of these genes, three of these genes, etc.). In further embodiments, the CD8+ memory T cell express elevated levels of each of the following genes: Ezh2, Hells, Bmi1, Survivin, p18Ink4c, and p21. In some embodiments, the contacting further comprises contacting the T-cells with IL-15 or IL-15 mimetic. In other embodiments, the contacting further comprises contacting the T-cells with lithium (e.g., chloride) or similar compound.

In certain embodiments, the antigen is a tumor-associated antigen, an infectious organism related antigen, or a self-antigen related to an autoimmune disease. In particular embodiments, the tumor-associated antigen is selected from the group consisting of anaplastic lymphoma kinase (ALK), ACRBP, BAGE, BCL-2, Tn218, carcino embryonic antigen (CEA), CD164, CD20, DNAJC2, EBAG9, ENOX2, ErbB 2, FATE1, FLT3-ITD, G250, GAGE1, Galectin 8, GPA33, GPNBB, HORMAD1, Her2, hTERT, IFITM2, LH39, LYK5, M2A oncofetal antigen, MAGE family antigens including but not limited to MAGE1, MAGE10, MAGE11, MAGE12, MAGEA2, MAGEA3, MAGEA4, MAGEA6, MAGEA8, MAGEA9, MAGEB18, MAGEB6, MABEC1, MAGED2, MAGEE1, MAGEH1, MAGEL2, MEL4, MelanA/MART1, melanoma associated antigen 100+, melanoma gp100, NRIP3, NYS48, OCIAD1, OFA-iLRP, OIP5, ovarian carcinoma-associated antigen (OV632), PAGE4, PARP9, PATE, plastin L, PRAME, prostate-specific antigen, proteinase 3, prostein, Reg3a, RHAMM, ROPN1, SART2, SDCCAG8, SEL1L, SEPT1, SLC45A2, SPANX, SSX5, STXGAL-NAC1, STEAP4, survivin, TBC1D2, TEM1, TRP1, tumor antigens of epithelial origin, XAGE1, XAGE2, and WT-1.

In particular embodiments, the methods further comprise administering the CD8+ memory T-cells to a subject. In some embodiments, the subject has a tumor and the contacting reduces the size (or eliminates) the tumor. In further embodiments, the subject is a human or domesticated animal. In other embodiments, the subject has a tumor expressing the antigen. In additional embodiments, the subject is further administered the antigen. In some embodiments, the subject is further administered IL-2 or IL-2 mimetic. In certain embodiments, the subject is further administered IL-15 or IL-15 mimetic. In other embodiments, the antigen specific memory T-cells are configured to persist in vivo for at least 8 weeks (e.g., at least 8 weeks . . . 12 weeks . . . 16 weeks . . . 45 weeks . . . or 52 weeks . . . 2 years or the lifetime of the subject). In certain embodiments, the cells persist in vivo between 8 and 25 weeks. In other embodiments, the mTOR pathway-inhibiting agent comprises rapamycin, rapamycin mimetic, or rapamycin analog. In certain embodiments, the mTOR pathway-inhibiting agents is selected from the group consisting of: rapamycin (sirolimus), CCI-779 (temsirolimus), everolimus (RAD-001), AP23573, a rapamycin analog (rapalog), mTOR antibodies, mTOR siRNAs, agents inhibiting mTOR phosphorylation, and combinations thereof. In some embodiments, the T-cell are human T-cells or a wild or domesticated animal T-cells.

In some embodiments, the present invention provides methods of treating a subject comprising: administering a composition to a subject, wherein the composition comprises isolated CD8+ memory T-cells specific for an antigen, wherein the isolated CD8+ memory T-cells are CD4410 and CD62Lhi, or CD44hi and CD62Lhi. In particular embodiments, the subject has a tumor expressing the antigen. In other embodiments, the subject is further administered the antigen or a vector encoding the antigen. In particular embodiments, the subject has a tumor and the contacting reduces the size (or eliminates) the tumor. In some embodiments, the subject is further administered IL-2 (or IL-2 mimetic) and/or IL-15 (or IL-15 mimetic). In other embodiments, the isolated CD8+ memory T-cells are ex vivo antigen-primed (and/or ex vivo cultured) CD8+ memory T-cells. In further embodiments, the isolated CD8+ memory T-cells are configured to persist in vivo for at least 8 weeks. In other embodiments, the composition further comprises a physiologically tolerable buffer. In additional embodiments, the composition further comprises an mTOR pathway inhibiting agent. In other embodiments, the composition further comprises the antigen or a vector encoding an antigen. In certain embodiments, the subject is further administered the antigen.

In some embodiments, the present invention provides compositions comprising: a) an mTOR pathway inhibiting agent (e.g., mTORC1 or mTORC2 pathway inhibiting agent), and b) isolated T-cells, wherein the T-cells are unprimed CD8+ T-cells. In other embodiments, the compositions further comprise at least one cytokine selected from IL-2 (or IL-2 mimetic) or IL-21 (or IL-21 mimetic). In particular embodiments, the compositions further comprise the antigen or a vector encoding the antigen. In further embodiments, the compositions further comprise antigen presenting cells. In other embodiments, the compositions further comprise culture media (e.g., ex vivo T-cell growth media). In particular embodiments, the mTOR pathway inhibiting agent inhibits mTOR function (e.g., mTOR activity, FRAP1/mTOR expression, mTOR protein level, mTOR stability).

In some embodiments, the present invention provides compositions comprising: a) an antigen, b) antigen-presenting cells, c) an mTOR pathway inhibiting agent (e.g., mTOR1 or mTOR2 pathway inhibiting agent), and d) isolated T-cells, wherein the T-cells are unprimed CD8+ T-cells. In particular embodiments, the compositions further comprise at least one cytokine, wherein the at least one cytokine is not produced by the isolated CD8+ memory T-cells. In additional embodiments, the at least one cytokine is IL-2 (or IL-2 mimetic) and/or IL-21 (or IL-21 mimetic). In further embodiments, the compositions further comprise ex vivo T-cell growth media.

In particular embodiments, the present invention provides compositions comprising: isolated CD8+ memory T-cells specific for an antigen, wherein the isolated CD8+ memory T-cells are CD4410 and CD62Lhi, or CD44hi and CD62Lhi. In some embodiments, the isolated CD8+ memory T-cells are ex vivo antigen-primed CD8+ memory T-cells. In further embodiments, the CD8+ memory T-cells are specific for a tumor-associated antigen. In other embodiments, the CD8+ memory T cell express elevated levels of at least one gene selected from the group consisting of: Ezh2, Hells, Bmi1, Survivin, p18Ink4c, and p21. In further embodiments, the CD8+ memory T cell express elevated levels of each of the following genes: Ezh2, Hells, Bmi1, Survivin, p18Ink4c, and p21. In additional embodiments, the isolated CD8+ memory T-cells are configured to persist in vivo for at least 8 weeks. In other embodiments, the compositions further comprise the antigen or a vector encoding the antigen. In some embodiments, the compositions further comprise an mTOR pathway inhibiting agent. In other embodiments, the compositions further comprise at least one cytokine not produced by the isolated CD8+ memory T-cells. In additional embodiments, the at least one cytokine is selected from IL-2 and IL-21 (or mimetics thereof). In other embodiments, the CD8+ memory T-cells are CD44$^{lo}$ and CD62L$^{hi}$. In further embodiments, the CD8+ memory T-cells are CD44$^{hi}$ and CD62L$^{hi}$. In some embodiments, the CD8+ memory T-cells are CD62L$^{hi}$. In particular embodiments, the compositions further comprise a physiologically tolerable buffer.

In some embodiments, the present invention provides systems comprising: a) an mTOR pathway inhibiting agent, and b) at least one cytokine selected from IL-2 and IL-21 (or mimetics thereof). In other embodiments, the systems further comprise T-cells, wherein the T-cells are unprimed CD8+ T-cells. In other embodiments, the systems further comprise a purified antigen or vector encoding an antigen. In certain embodiments, the systems further comprise antigen-presenting cells.

In further embodiments, the present invention provides systems comprising: a) an mTOR pathway inhibiting agent, and b) T-cells, wherein the T-cells are unprimed CD8+ T-cells.

In some embodiments, the present invention provides systems comprising: a) a composition comprising isolated CD8+ memory T-cells specific for an antigen, wherein the isolated CD8+ memory T-cells are CD44lo and CD62Lhi, or CD44hi and CD62Lhi; and b) a device for administering the composition to a subject, wherein the composition is located within the device. In other embodiments, the isolated CD8+ memory T-cells are ex vivo antigen-primed CD8+ memory T-cells. In further embodiments, the device comprises a syringe.

In particular embodiments, the present invention provides systems comprising: a) a composition comprising isolated CD8+ memory T-cells specific for an antigen, wherein the isolated CD8+ memory T-cells are CD44lo and CD62Lhi, or CD44hi and CD62Lhi; and b) a syringe vial, wherein the composition is located within the syringe vial.

In other embodiments, the present invention provides systems comprising: a) a composition comprising isolated CD8+ memory T-cells specific for an antigen, wherein the isolated CD8+ memory T-cells are CD44lo and CD62Lhi, or CD44hi and CD62Lhi; and b) a component selected from; the antigen, IL-2 (or mimetic thereof), and IL-15 (or mimetic thereof). In additional embodiments, the CD8+ memory T-cells have the ability to generate both effector and memory T cells upon secondary challenge of the antigen.

In some embodiments, the present invention provides compositions comprising ex vivo culture-generated CD8+ memory T cells capable of prolonged proliferation in vivo. In particular embodiments, the prolonged proliferation in vivo is for a period of at least 8 weeks. In other embodiments, the CD8+ memory T cells are IFN-γhi granzyme Bhi CD44hi CD62Llo CCR7lo CD8+ T cells. In further embodiments, the CD8+ memory T cells are tumor-reactive. In particular embodiments, the CD8+ memory T cells have been stimulated by at least one tumor-specific or tumor-associated antigen.

DEFINITIONS

Figure 1:
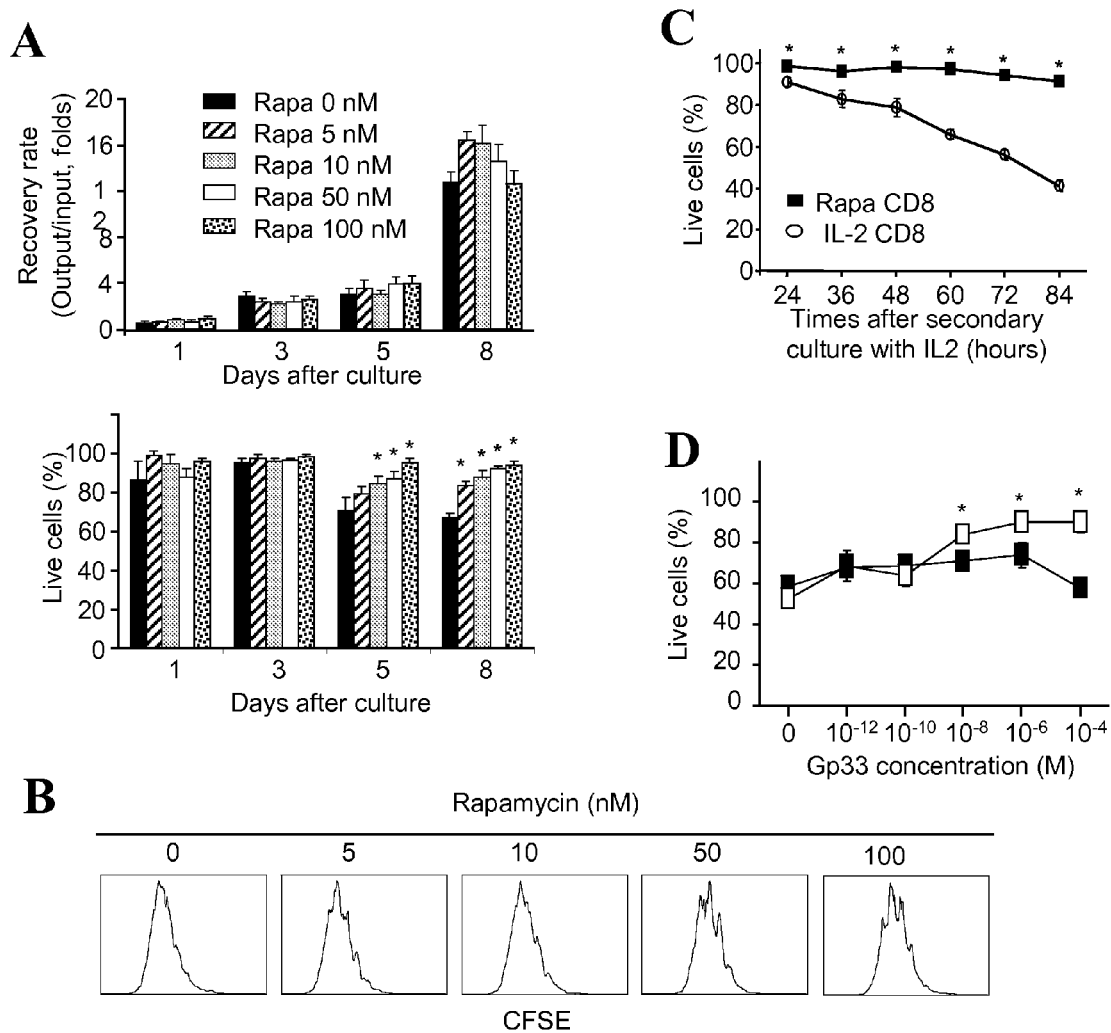
FIG. 1 shows rapamycin induces in vitro antigen-primed CD8+ T cells with intact ability to divide and proliferate but higher survival capability. P14 naive CD44loCD8+ T cells were pre-stained with CFSE and primed in vitro with B6-derived DCs pulsed with 10-7 M gp33, in conjunction with 5 ng/ml IL-2 (named IL-2 CD8+ T cells) and titrated doses of rapamycin (named Rapa CD8+ T cells) for 6 days. (A) Cells recovered at indicated time points from cultures were stained with the trypan blue and counted using light microscope. Live cell ratio=Trpan blue negative cell number/total cell number× 100%. (B) Six days after culture, cells were collected for flow cytometry analysis. Histograms show CFSE intensity of activated CD8+ T cells cultured in the presence of different concentration of rapamycin. (C) IL-2 CD8+ T cells and Rapa CD8+ T cells were collected six days after culture, washed twice to remove the rapamycin and further cultured in secondary cultures in the absence of IL-2 over a period of 84 hours. Cells were recovered at the indicated time points and counted to calculate live cell ratio. (D) P14 naive CD44loCD8+ T cells were cultured in the presence of different concentrations of gp33 peptide as indicated, with or without addition of rapamycin (50 nM). Cells were recovered, counted and calculated for live cell ratio. Data are shown as means±SD and representative from five independently performed experiments. *p<0.05.

To facilitate an understanding of the present invention, a number of terms and phrases are defined below:

As used herein, the term "mTOR pathway," "mTOR signaling pathway," or "mTOR associated pathway" refers generally to biological (e.g., molecular, genetic, cellular, biochemical, pharmaceutical, environmental) events (e.g., cellular pathways, cellular mechanisms, cellular cascades) involving the mTOR gene and/or the mTOR protein. Examples of components of the mTOR pathway include, but are not limited to, TSC-1, TSC-2, TSC-1/TSC-2 complex, raptor, rictor, GβL, FKBP12, Rheb, mTOR, S6K, and 4EBP-1.

As used herein, the term "mTOR function" refers generally to any type of cellular event for which mTOR is involved (e.g., DNA based activity, mRNA based activity, protein based activity; phosphorylation; associated pathway activity) (e.g., mTOR activity, FRAP1/mTOR expression, mTOR protein level, mTOR stability).

As used herein, the terms "anticancer agent," "conventional anticancer agent," or "cancer therapeutic drug" refer to any therapeutic agents (e.g., chemotherapeutic compounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

An "effective amount" is an amount sufficient to effect beneficial or desired results. An effective amount can be administered in one or more administrations.

As used herein, the term "administration" refers to the act of giving a drug, prodrug, antibody, or other agent, or therapeutic treatment to a physiological system (e.g., a subject or in vivo, in vitro, or ex vivo cells, tissues, and organs). Exemplary routes of administration to the human body can be through the eyes (opthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Coadministration" refers to administration of more than one chemical agent or therapeutic treatment to a physiological system (e.g., a subject or in vivo, in vitro, or ex vivo cells, tissues, and organs). "Coadministration" of the antigen-specific memory T-cells and drug compounds may be concurrent, or in any temporal order or physical combination.

As used herein, the term "regression" refers to the return of a diseased subject, cell, tissue, or organ to a non-pathological, or less pathological state as compared to basal nonpathogenic exemplary subject, cell, tissue, or organ. For example, regression of a tumor includes a reduction of tumor mass as well as complete disappearance of a tumor or tumors.

As used herein the term, "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reactions that occur within a natural environment.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "subject" or "patient" refers to organisms to be treated by the methods of the present invention. Such organisms include, but are not limited to, humans and veterinary animals (dogs, cats, horses, pigs, cattle, sheep, goats, and the like). In the context of the invention, the term "subject" or "patient" generally refers to an individual who will receive or who has received treatment.

The term "diagnosed," as used herein, refers to the recognition of a disease by its signs and symptoms or genetic analysis, pathological analysis, histological analysis, and the like.

DETAILED DESCRIPTION OF THE INVENTION

The present invention provides compositions, methods, and systems for generating antigen-specific long-term memory T-cells using mTOR pathway inhibitors. The present invention provides compositions, systems, and methods for administering antigen-specific long-term memory T-cells to a subject (e.g., to a subject with cancer in adoptive transfer type of procedures).

Antigen-presenting cell (APC) activation of naïve T cells induces the generation of effector and memory T cells (Kaesch et al., Nat. Rev. Immunol., 2:251-262, 2002; Lanzavecchia et al., Curr. Opin. Immunol., 17:326-332, 2005; Lefrancois et al., Nat. Rev. Immunol., 6:618-623, 2006; each herein incorporated by reference in its entirety). Effector T cells mediate acute elimination of pathogens but are short-lived cells owing to programmed death. Memory T cells can survive the life time of an individual via a self-renewing mechanism, i.e. proliferation without differentiation. Upon re-exposure to the cognate antigen, memory T cells can rapidly elaborate effector functions, providing long-term protection against pathogens (Fearon et al., Science, 293:248-250, 2001; Lanzavecchia et al., Nat. Rev. Immunol., 2:982-987, 2002; Reiner et al., Science, 317:622-625, 2007; Luckey et al., PNAS, 103:3304-3309, 2006; each herein incorporated by reference in its entirety). Thus, generation of long-term memory T cells is the ultimate goal for efficacious adoptive T cell immunotherapy and represents a key unmet need prior to development of embodiments of the present invention (Lefrancois et al., Nat. Rev. Immunol., 6:618-623, 2006; Lanzavecchia et al., Nat. Rev. Immunol., 2:982-987, 2002; Reiner et al., Science, 317:622-625, 2007; Fearon et al., Immunol. Rev., 211:104-118, 2008; Hinrichs et al., Curr. Opin. Immunol., 18:363-370, 2006; June, J. Clin. Invest., 117:1466-1476, 2007; June, J. Clin. Invest., 117:1204-1212, 2007; Kaech et al., Cell, 111:837-851, 2002; Masopust et al., Curr. Opin. Immunol., 16:217-225, 2004; Rosenberg, New Engl. J. Med., 350:1361-1463, 2004; Wherry et al., Nat. Immunol., 4:225-234, 2004; each herein incorporated by reference in its entirety). On the other hand, memory T cells have proven problematic in T cell-mediated inflammatory disorders, such as graft-versus-host disease (GVHD) after allogeneic hematopoietic stem cell transplantation (HSCT). GVHD remains the major cause of morbidity and mortality after allogeneic HSCT and has hampered the application of allogeneic HSCT (Blazar et al., Philos. Trans. R. Soc. Lond. B. Biol. Sci., 360:1747-1787, 2005; Ferrara et al., Int. J. Hematol., 78:181-187, 2003; Goker et al., Exp. Hematol., 29:259-277, 2001; Ho et al., Blood, 98:3192-3204, 2001; Wu et al., Adv. Immunol., 90:133-173, 2006; each herein incorporated by reference in its entirety). Studies have recently demonstrated that alloreactive memory T cells are responsible for the persistence and perhaps the progression of GVHD (Dutt et al., J. Immunol., 179:6547-6554, 2007; Yamashita et al., Blood, 103:3986-3988, 2004; Zhang et al., J. Immunol., 174:3051-3058, 2005; Zhang et al., Nat. Med., 11:1299-1305, 2005; each herein incorporated by reference in its entirety). Therefore, while the present invention is not limited to any particular mechanism, and an understanding of the mechanism is not necessary to practice the present invention, better understanding the mechanisms that regulate memory T cells has significant clinical implications.

Memory $CD8^+$ T cells are cells at an arrested differentiation stage of proliferating T cells driven by antigenic stimulation (Kaesch et al., Nat. Rev. Immunol., 2:251-262, 2002; Lanzavecchia et al., Curr. Opin. Immunol., 17:326-332, 2005; Lanzavecchia et al., Nat. Rev. Immunol., 2:982-987, 2002; Wherry et al., Nat. Immunol., 4:224-234, 2003, Wherry et al., Immunity, 27:670-684, 2007; Sallusto et al., Nature, 401:708-712, 1999, all of which are herein incorporated by reference). Studies in mouse models of GVHD have previously identified that $CD44^{lo}CD62L^{hi}CD8^+$ postmitotic T cells ($T_{PM}$) have greater ability than $CD44^{hi}CD62L^{hi}$ central memory-phenotype T cells ($T_{CM}$) and $CD44^{hi}CD62L^{lo}$ effector memory-phenotype T cells ($T_{EM}$) to proliferate, while self-renewing. They are not cytolytic cells, but can cause GVHD when adoptively transferred into secondary recipients (Zhang et al., Nat. Med., 11:1299-1305, 2005; herein incorporated by reference in its entirety). Therefore alloreactive $CD8^+$ $T_{PM}$ are cells at the early stage of effector differentiation. Antigen-experienced $CD8^+$ T cells bearing the phenotype of $T_{PM}$ occur in varieties of immune responses against pathogens and tumor antigens. For instance, antigen-primed $CD8^+$ T cells undergoing their first asymmetric division generated two distinct subsets, i.e. $CD44^{hi}CD62L^{lo}$ proximal daughter cells and $CD44^{lo/mod}CD62L^{hi}$ distal daughter cells. Among them, only the distal daughter cells can generate both effector cells and long-lasting memory T cells (Chang et al, Science, 315:1687-1691, 2007; herein incorporated by reference in its entirety). Although it has yet to be determined whether $CD8^+$ $T_{PM}$ developed in GVHD mouse models are closely related to those of distal $CD8^+$ T daughter cells at the phenotypic and transcriptional levels, it is clear that both can generate memory T cells (Zhang et al., Nat. Med., 11:1299-1305, 2005; Chang et al, Science, 315:1687-1691, 2007; each herein incorporated by reference in its entirety). Additionally, $CD8^+$ T cells $T_{PM}$ developed in an ex vivo culture in the presence of IL-21 have potent anti-tumor activity upon adoptive transfer into tumor-bearing mice (Hinrichs et al., Blood, 111:5326-5333, 2008; Zeng et al., J. Exp. Med., 201:139-148, 2005; each herein incorporated by reference in its entirety). Thus, while the present invention is not limited to any particular mechanism, and an understanding of the mechanism is not necessary to practice the present invention, identification of CD8+ T$_{PM}$ offers an opportunity to better understand the cellular and molecular mechanisms that regulate the generation of memory T cells.

Memory CD8+ T cells are stem cell-like cells. They have acquired several features of stem cells, i.e. the ability to self-renew and the capability to proliferate and to generate differentiated effector cells (Fearon et al., Science, 293:248-250, 2001; Lanzavecchia et al., Nat. Rev. Immunol., 2:982-987, 2002; Hinrichs et al., Curr. Opin. Immunol., 18:363-370, 2006; Fearon et al., Immunol. Rev., 211:104-118, 2006; Hinrichs et al., Blood, 111:5326-5333, 2008; each herein incorporated by reference in its entirety). This is further supported by gene array assays that memory CD8+ T cells share some similar transcriptional profiles to long-term hematopoietic stem cells (HSC) (Luckey et al., PNAS, 103:3304-3309, 2006; herein incorporated by reference in its entirety). Therefore, signals functioning in HSCs are engaged in the development of memory CD8+ T cells. At least two molecules that are important for maintaining quiescence and function of HSCs are down-stream targets of TCR triggering/CD28 co-stimulation (Kane et al., Immunol. Rev., 192:7-20, 2003; herein incorporated by reference in its entirety): mammalian target of rapamycin (mTOR) (Chen et al., J. Exp. Med., 205:2397-2408, 2008; herein incorporated by reference in its entirety) and glycogen synthesis kinase 3 (GSK3) (Sato et al., Nat. Med., 10:55-63, 2004; Reya et al., Nature, 434:843-850, 2005; Trowbridge et al., Nat. Med., 12:89-98, 2006; each herein incorporated by reference in its entirety). The prior art remains silent on whether GSK3 and mTOR are important for the generation of memory T cells from proliferating CD8+ T cells.

Using alloreactive T cells activated by alloantigens and TCR transgenic P14 CD8+ T cells specific to lymphocytic choriomeningitis virus gp33 peptide, antigen-primed CD8+ T cells were demonstrated during experiments conducted during the course of developing certain embodiments of the present invention to initially give rise to 3 distinct subsets, including T$_{PM}$, T$_{CM}$ and T$_{EM}$. Analysis of transcriptome profiling data revealed that CD8+ T$_{PM}$ and T$_{EM}$ represent undifferentiated and fully differentiated cells, respectively. Built on this analysis, quantitative real-time RT-PCT (qRT-PCR) analysis was used to demonstrate that T$_{CM}$ represented cells at the intermediate differentiation stage between T$_{PM}$ and T$_{EM}$. Reducing antigenic stimulation enhanced the generation of less differentiated T$_{PM}$ and T$_{CM}$. Interestingly, inactivation of mTOR1 during the antigenic priming phase polarized the generation of T$_{CM}$ from proliferating CD8+ T cells by suppressing their effector differentiation, whereas inactivation of GSK3 induces the effector differentiation of these T$_{CM}$. Thus, the present invention demonstrates that manipulation of antigen-activated CD8+ T cell differentiation during the antigenic-priming phase via regulating mTOR and GSK3 has significant implications in controlling memory T cell responses.

The present invention provides approaches to generate sufficient numbers of tumor-reactive T cells that can persist for a long time in vivo for destroying tumors. During development of embodiments of the present invention, unprimed CD8+ T cells from normal wild type mice were obtained, which contain a low frequency of tumor reactive CD8+ precursor T cells. These cells generally require professional antigen presenting cells and cytokine for their activation, proliferation and functional differentiation into tumor-reactive effector and memory T cells. To generate sufficient numbers of tumor-reactive memory T cells, these cells were stimulated repeatedly with tumor-associated antigen pulsed antigen presenting cells to expand the tumor-reactive T cell pool. In normal mice, CD8+ T cells are originally obtained from the spleens and lymph nodes, which are termed unprimed CD8+ T cells. These unprimed CD8+ T cells are polyclonal T cells that are composed of up to $10^6$ different T cell clones. Each clone recognizes and reacts to one specific antigen. However, unprimed CD8+ T cells contain low frequency of precursor T cells (estimated to be between 100 and 1000 cells per mouse) reactive to one specific tumor antigen, such as self-antigen and tumor-associated antigen. Upon the antigenic stimulation, these CD8+ T cells were induced to proliferate and differentiate into effector cells, mediating potent immune response against targets expressing the specific antigen. In a typical immune response against pathogen, e.g. virus infection, an antigen-specific T cell clone can expand more than 100,000 fold over period of 7 to 14 days after antigenic stimulation in order for the host to eliminate the pathogen.

In certain embodiments, CD8+ T cells are obtained from the peripheral blood of human donors (e.g., cancer patients and healthy donors). Using the established culture system, human CD8+ T cells are repeatedly stimulated with tumor-associated antigens to generate tumor-reactive T cells that can persist after their adoptive transfer. In humans, CD8+ T cells can be obtained from peripheral blood. Unlike mice grown in a pathogen-free environment, human beings have been exposed to antigens in the environment and vaccinations. Thus, CD8+ T cells from human beings display high heterogeneity, consisting of both unprimed CD8+ T cells and primed CD8+ T cells that react to a milieu of known and unknown antigens. The frequency of unprimed CD8+ T cells that can potentially recognize and react to self-antigen and tumor associated antigens is very low. Thus, repeated (multiple rounds of) stimulation of unprimed T cells with tumor associated antigens, without inducing terminal differentiation, may be important in certain embodiments to increase the frequency of tumor-reactive T cells.

During experiments conducted during the course of developing certain embodiments of the present invention, an ex vivo culture method was developed to generate the precursors of long-lasting memory T cells (e.g., for T cell adoptive immunotherapy). In certain embodiments, this culture system included T cells, antigen-presenting cells, antigens (tumor cell lysates, proteins, and peptides), IL-2 and rapamycin. In some circumstance, IL-15 and IL-21 were added to further increase the frequency of tumor-reactive T cells that have great ability to generate long-lasting memory T cells in vivo following adoptive transfer.

T cells can be obtained, for example, from the spleen and lymph node of normal mice and from the peripheral blood of humans. These T cells can be naïve T cells that have never been primed by the specific antigens used in the culture system, or antigen-experienced T cells that have been stimulated by the specific antigens in vivo.

Antigen presenting cells used in this culture system include, for example, dendritic cells and mitogen-activated immune cells. These antigen presenting cells can be derived, for example, from cultured bone marrow or blood leukocytes and immune cells. In certain embodiments, these antigen-presenting cells express high levels of co-stimulatory molecules such as CD86, CD40 and 4-1BBL, which can be important for inducing the generation of precursors for long-lasting memory T cells. In some embodiments, cytokines, such as IL-2, IL-15 and IL-21, are added into the culture to stimulate the expansion of tumor-reactive T cells, thereby increasing the frequency of tumor-reactive T cell precursors.

An mTOR pathway inhibitor (e.g., mTOR1 or mTOR2 pathway inhibiting agent), such as rapamycin, is an important factor to generate precursors for long-lasting tumor-reactive T cells. Since rapamycin specifically inhibits the signaling pathway mTOR1, any other inhibitors that modulate mTOR1 pathway (upstream or downstream) have a similar impact on the generation of tumor-reactive T cell precursors of long lasting memory T cells and are contemplated for use by the present invention. Agents that inhibit mTOR include rapamycin (sirolimus), CCI-779 (temsirolimus), everolimus (RAD-001), AP23573, rapamycin analogs (rapalogs), mTOR antibodies, mTOR siRNAs, agents inhibiting mTOR phosphorylation, agents inhibiting interaction of mTOR with its partners, and agents inhibiting interaction of mTOR with its substrates.

These memory T cell precursors display stem cell-like properties, i.e. the ability to self-renew and the capability to continually generate differentiated effector T cells that attack the targets. This effect of rapamycin on the generation of long-lasting memory precursor T cells results from its effects on augmenting the self-renewal of stem cells. Thus, mTOR pathway inhibitors, such as rapamycin, are not only important for the initial antigenic-priming of naïve T cells in the culture, but also important, in certain embodiments, for sustaining the stem cell-like property of antigen-activated T cells during multiple rounds of antigenic stimulation.

The combination of mTOR pathway inhibitors (e.g., rapamycin) and various cytokines induces different populations of tumor-reactive precursors of long lasting memory T cells. For example, the combination of rapamycin and IL-2 predominantly induces the generation of central memory like T cells, which can be further augmented by addition of IL-15. In contrast, the combination of rapamycin and IL-21 induces the generation of memory stem cell-like phenotype ($CD44^{lo}CD62L^{hi}Sca-1^{hi}CD122^{hi}CD127^{hi}Bcl-2^{hi}$). These cells have greater ability than central memory-like T cells to proliferate and survive, thereby enhancing the anti-antigen (e.g., anti-tumor) activity in vivo after their adoptive transfer. Thus, both central memory-like T cells and memory stem cell-like cells are generated in some culture system embodiments of the present invention and can be used for augmenting adoptive T cell immunotherapy in some methods of the present invention.

In certain embodiments, after a subject has been treated with the adoptive transfer methods and compositions of the present invention, diagnostic procedures are employed to determine efficacy. In certain embodiments, tumor regression is analyzed. For example, clinical and radiographic responses (e.g. MRI and CT) can be used for monitoring the effector tumor-reactive T cells on tumor growth. Certain procedures include clinical, histological and bioluminescent in vivo imaging for monitoring tumor growth. In some embodiments, the persistence of functional tumor-reactive T-cells is monitored. For example, antigen peptide/MHC-I tetramer technique and intracellular staining and ELISPOT assay of IFN-γ producing cells can be used for testing the frequency and persistence of tumor-reactive T cells. In other embodiments, the recall response of infused tumor-reactive T cells can be monitored. Ex vivo culture in the presence of antigen-presenting cells pulsed with antigen peptides can be used to examine the ability of infused tumor-reactive T cells to respond to the restimulation of the specific antigen. This method is used to measure the proliferation, effector differentiation and survival of recovered tumor-reactive T cells upon the antigenic restimulation.

In particular embodiments, assays are employed to determine if long-lasing memory T-cells are generated with the compositions and methods disclosed herein. In some embodiments, a phenotypic based assay is employed. For example, long lasting memory T cell precursors that are generated in the ex vivo culture system express central memory like-phenotype (CD44hiCD62Lhi) and memory stem cell-like phenotype (CD44loCD62LhiSca-1hiCD122hiCD127hiBcl-2hi). Both of these T cell subsets are antigen-activated T cells, expressing high levels of CD122 but low levels of IFN. Phenotypically, they can be distinguished from short-lived antigen-activated T cells expressing the phenotype of CD44hiCD62Llo. Flow cytometry analysis or other techniques can be used for measuring cell phenotype. In further embodiments, a genotype type monitoring is employed that is based on the expression of stem cell signals. For example, long-lasting memory T cells that are generated in the culture systems disclosed herein increase the expression of genes that are enriched in stem cells for stimulating the proliferation and self-renewal of stem cells, such as Ezh2, Hells, Bmi1, Survivin, p18Ink4c and p21. As compared to short-lived T cells generated from conventional cultures, increased expression of these genes indicates the generation of long-lasting memory T cells. Real-time PCR or other techniques can be used for measuring the gene expression. In further embodiments functional assays based on the ability to respond to antigenic stimulation are employed to monitor the results of ex vivo culturing. For example, repeated antigenic stimulation can be used for assessing whether memory T cell precursors generated in ex vivo cultures are able to persist in vivo after adoptive transfer. The specific antigen peptides and antigen-presenting cells may be added, for example, every 5 days into the culture containing memory T cell precursors. After 3 rounds of antigenic stimulation, cells may be recovered from the culture to measure: i) numbers of live cells; ii) number of cells producing IFN-γ; iii) and number of cells with cytolytic effect against the cognate tumor cells.

mTOR Pathway Inhibitors

The present invention is not limited by the type of mTOR pathway inhibiting agent used in the methods, compositions, and systems of the present invention. mTOR, is a serine/threonine protein kinase that regulates cell growth, cell proliferation, cell motility, cell survival, protein synthesis, and transcription (see, e.g., Hay N, et al. (2004) Genes & Development, 18(16): 1926-45; Beevers C S, et al. (2006) International Journal of Cancer, 119(4):757-64; each herein incorporated by reference in their entireties), mTOR integrates input from multiple upstream pathways, including insulin, growth factors (such as IGF-1 and IGF-2), and mitogens (see, e.g., Hay N, et al. (2004) Genes & Development, 18(16): 1926-45; herein incorporated by reference in its entirety), mTOR also functions as a sensor of cellular nutrient and energy levels and redox status (see, e.g., Hay N, et al. (2004) Genes & Development, 18(16): 1926-45; Tokunaga C, et al. (2004) Biochemical and Biophysical Research Communications, 313:443-46; Sarbassov D D, et al. (2005) Journal of Biological Chemistry, 280(47):39505-509; each herein incorporated by reference in their entireties). The dysregulation of the mTOR pathway is implicated as a contributing factor to various human disease processes (see, e.g., Beevers C S, et al. (2006) International Journal of Cancer, 119(4):757-64; herein incorporated by reference in its entirety), including but not limited to TSC, epilepsy and diabetes. Rapamycin is a bacterial natural product that can inhibit mTOR through association with its intracellular receptor FKBP12 (see, e.g., Huang S, et al. (2001) Drug Resistance Updates, 4:378-91; Huang S, et al. (2003) Cancer Biology and Therapy, 2:222-232; each herein incorporated by reference in its entirety). The FKBP 12-rapamycin complex binds directly to the FKBP 12-Rapamycin Binding (FRB) domain of mTOR (see, e.g., Huang S, et al. (2003) Cancer Biology and Therapy, 2:222-232; incorporated herein by reference in its entirety).

mTOR has been shown to function as the catalytic subunit of two distinct molecular complexes in cells (see, e.g., Wullschleger S, et al. (2006) Cell, 124(3):471-84; incorporated herein by reference in its entirety), mTOR Complex 1 (mTORC1) is composed of mTOR, regulatory associated protein of mTOR (Raptor), and mammalian LST8/G-protein β3-subunit like protein (mLST8/GβL) (see, e.g., Kim D H, et al. (2002) Cell, 110:163-75; Kim D H, et al. (2003) Molecular Cell, 11:895-904; each incorporated herein by reference in their entireties). This complex possesses the classic features of mTOR by functioning as a nutrient/energy/redox sensor and controlling protein synthesis (see, e.g., Kim D H, et al. (2002) Cell, 110:163-75; Hay N, et al. (2004) Genes & Development, 18(16): 1926-45; each incorporated herein by reference in their entireties). The activity of this complex is stimulated by insulin, growth factors, serum, phosphatidic acid, amino acids (particularly leucine), and oxidative stress (see, e.g., Kim D H, et al. (2002) Cell, 110:163-75; Sarbassov D D, et al. (2005) Journal of Biological Chemistry, 280(47):39505-509; Fang Y, et al. (2001) Science, 294:1942-45; each incorporated herein by reference in their entireties), mTORC 1 is inhibited by low nutrient/amino acid levels, serum-starvation/growth factor deprivation, reductive stress, and caffeine, rapamycin, farnesylthiosalicylic acid (FTS) and curcumin (see, e.g., Kim D H, et al. (2002) Cell, 110:163-75; Sarbassov D D, et al. (2005) Journal of Biological Chemistry, 280(47): 39505-509; McMahon L P, et al. (2005) Molecular Endocrinology, 19(1): 175-83; Beevers C S, et al. (2006) International Journal of Cancer, 119(4):757-64; each incorporated herein by reference in their entireties). Two characterized targets of mTORC 1 are p70-S6 Kinase 1 (S6K1) and eukaryotic initiation factor 4E (eIF4E) binding protein 1 (4E-BP1) (see, e.g., Hay N, et al. (2004) Genes & Development, 18 (16): 1926-45; incorporated herein by reference in its entirety), mTORC 1 phosphorylates S6K1 on at least two residues, with the most critical modification occurring on threonine-389 (see, e.g., Saitoh M, et al. (2002) Journal of Biological Chemistry, 277:20104-112; Pullen N, et al. (1997) FEBS Letters, 410:78-82; incorporated herein by reference in its entirety). This event stimulates the subsequent phosphorylation of S6K1 by PDK1 (see, e.g., Pullen N, et al. (1997) FEBS Letters, 410:78-82; Pullen N, et al. (1998) Science, 279:707-10; each incorporated herein by reference in their entireties). Active S6K1 can in turn stimulate the initiation of protein synthesis through activation of S6 Ribosomal protein (a component of the ribosome) and other components of the translational machinery (see, e.g., Peterson R, et al. (1998) Current Biology, 8:R248-50; incorporated herein by reference in its entirety). S6K1 can also participate in a positive feedback loop with mTORC 1 by phosphorylating mTOR's negative regulatory domain at threonine2446 and serine2448, events which appear to be stimulatory in regards to mTOR activity (see, e.g., Chiang G G, et al. (2005) Journal of Biological Chemistry, 280:25485-90; Holz M K, et al. (2005) Journal of Biological Chemistry, 280:26089-93; each incorporated herein by reference in their entireties), mTORC 1 has been shown to phosphorylate at least four residues of 4E-BP1 in a hierarchial manner (see, e.g., Gingras A C, et al. (1999) Genes & Development, 13:1422-37; Huang S, et al. (2001) Drug Resistance Updates, 4:378-91; Mothe-Satney I, et al. (2000) Journal of Biological Chemistry, 275:33836-43; each incorporated herein by reference in their entireties). Non-phosphorylated 4E-BP1 binds tightly to the translation initiation factor eIF4E, preventing it from binding to 5'-capped mRNAs and recruiting them to the ribosomal initiation complex (see, e.g., Hay N, et al. (2004) Genes & Development, 18(16): 1926-45; Pause A, et al. (1994) Nature, 371:762-67; each incorporated herein by reference in their entireties). Upon phosphorylation by mTORC 1, 4E-BP1 releases eIF4E, allowing it to perform its function (see, e.g., Pause A, et al. (1994) Nature, 371:762-67; incorporated herein by reference in its entirety). The activity of mTORC 1 appears to be regulated through a dynamic interaction between mTOR and Raptor, one which is mediated by GβL (see, e.g., Kim D H, et al. (2002) Cell, 110:163-75; Kim D H, et al. (2003) Molecular Cell, 11:895-904; each incorporated herein by reference in their entireties). Raptor and mTOR share a strong N-terminal interaction and a weaker C-terminal interaction near mTOR's kinase domain (see, e.g., Kim D H, et al. (2002) Cell, 110: 163-75; incorporated herein by reference in its entirety). When stimulatory signals are sensed, such as high nutrient/energy levels, the mTOR-Raptor C-terminal interaction is weakened, allowing mTOR kinase activity to be turned on (see, e.g., Kim D H, et al. (2002) Cell, 110:163-75; incorporated herein by reference in its entirety). When stimulatory signals are withdrawn, such as low nutrient/energy levels, the mTOR-Raptor C-terminal interaction is strengthened, essentially shutting off mTOR kinase function (see, e.g., Kim D H, et al. (2002) Cell, 110:163-75; incorporated herein by reference in its entirety).

mTOR Complex 2 (mTORC2) is composed of mTOR, rapamycin-insensitive companion of mTOR (Rictor), GβL, and mammalian stress-activated protein kinase interacting protein 1 (mSIN1) (see, e.g., Frias M A, et al. (2006) Current Biology, 16(18):1865-70; Sarbassov D D, et al. (2004) Current Biology, 14:1296-1302; each incorporated herein by reference in their entireties). mTORC2 has been shown to function as an important regulator of the cytoskeleton through its stimulation of F-actin stress fibers, paxillin, RhoA, Racl, Cdc42, and protein kinase C α (PKCα) (see, e.g., Sarbassov D D, et al. (2004) Current Biology, 14:1296-1302; incorporated herein by reference in its entirety). However, an unexpected function of mTORC2 is its role as "PDK2." mTORC2 phosphorylates the serine/threonine protein kinase Akt/PKB at serine473, an event which stimulates Akt phosphorylation at threonine308 by PDK1 and leads to full Akt activation (see, e.g., Sarbassov D D, et al. (2004) Current Biology, 14:1296-1302; Stephens L, et al. (1998) Science, 279:710; each incorporated herein by reference in their entireties), mTORC2 appears to be regulated by insulin, growth factors, serum, and nutrient levels (see, e.g., Frias M A, et al. (2006) Current Biology, 16(18): 1865-70; incorporated herein by reference in its entirety). Originally, mTORC2 was identified as a rapamycin-insensitive entity, as acute exposure to rapamycin did not affect mTORC2 activity or Akt phosphorylation (see, e.g., Sarbassov D D, et al. (2004) Current Biology, 14:1296-1302; Sarbassov D D, et al. (2005) Science, 307:1098-1101; each incorporated herein by reference in their entireties). However, subsequent studies have shown that chronic exposure to rapamycin, while not effecting pre-existing mTORC2s, can bind to free mTOR molecules, thus inhibiting the formation of new Complex 2s (see, e.g., Sarbassov D D, et al. (2006) Molecular Cell, 22(2): 159-68; incorporated herein by reference in its entirety). It has also been shown that curcumin can inhibit the mTORC2-mediated phosphorylation of Akt/PKB at serine473, with subsequent loss of PDK1-mediated phosphorylation at threonine308 (see, e.g., Beevers C S, et al. (2006) International Journal of Cancer, 119(4):757-64; incorporated herein by reference in its entirety).

The present invention provides agents capable of inhibiting mTOR function (e.g., mTOR activity, FRAP1/mTOR expression, mTOR protein level, mTOR stability). The present invention is not limited to a particular type of agent capable of inhibiting mTOR expression. In some embodiments, the mTOR inhibiting agent is an agent that inhibits any part of the pathways associated with mTOR function (e.g., mTOR activity, FRAP1/mTOR expression, mTOR protein level, mTOR stability) (e.g., IRS1, PI3K, PDK1, Akt, PKC, Rac, Rho, LKB1, Rheb, FKBP, mTOR, mLST8/GβL, S6K, S6, 4EBP1, rS6, eIF4E, eIF3, eIF4A, eIF4G, eIF4B, raptor, Vps34, rictor, PTEN, GSK3, LKB1, AMPK, RTP801/L, HIF1, REDD1, TSC1, TSC2). In some embodiments, the mTOR inhibiting agent is rapamycin and rapamycin derivatives. In some embodiments, the mTOR inhibiting agent is rapamycin (sirolimus), CCI-779 (temsirolimus), everolimus (RAD-001), AP23573, rapamycin analogs (rapalogs), mTOR antibodies, mTOR siRNAs, agents inhibiting mTOR phosphorylation, agents inhibiting interaction of mTOR with its partners, or agents inhibiting interaction of mTOR with its substrates.

Rapamycin (sirolimus (RAPAMUNE)) is a commercially available immunosuppressant that forms an inhibitory complex with the immunophilin FKBP12, which then binds to and inhibits the ability of mTOR to phosphorylate downstream substrates, such as the S6Ks and 4EBPs. It is marketed as an immunosuppressant because of its propensity to inhibit T-cell proliferation, and has been approved for use in this therapeutic setting in the United States since 2001. Two derivatives of rapamycin, RAD001 (everolimus (CERTICAN)) and a prodrug for rapamycin, CCI-779 or temsirolimus, are in clinical development in a number of therapeutic indications, including oncology (see, e.g., Chapman T, et al., Drugs 2004:64:861-872; Temsirolimus: CCI 779, CCI-779, cell cycle inhibitor-779. Drugs RD 2004; 5: 363-367; each herein incorporated by reference in their entireties). Animal studies have demonstrated the ability of rapamycin to inhibit the aberrant growth of TSC-deficient cells in vitro and to induce apoptosis of renal tumors in animal models of TSC (see, e.g., Kenerson H, et al., Pediatr Res 2005; 57: 67-75; herein incorporated by reference in its entirety).

In some embodiments, the present invention provides compositions for culturing unprimed CD8+ cells with an mTOR inhibiting agent, as well as antigen, to generate antigen-specific long-term CD8+ memory T-cells. In certain embodiments, the mTOR inhibiting agent is selected from rapamycin (sirolimus), CCI-779 (temsirolimus), everolimus (RAD-001), AP23573, rapamycin analogs (rapalogs), mTOR antibodies, mTOR siRNAs, agents inhibiting mTOR phosphorylation, agents inhibiting interaction of mTOR with its partners, agents inhibiting interaction of mTOR with its substrates. Additional mTOR inhibitors for use with the present invention are provided in U.S. Pat. Pub. 20080255029; U.S. Pat. Pub. 20080207644; U.S. Pat. Pub. 20090012105; and WO2007106503, all of which are herein incorporated by reference as if fully set forth herein.

Administration and Dosing Regimes

One skilled in the art will appreciate that administration and dosing of cells for adoptive transfer may need to be customized to the patient for highest efficacy and tolerance. Tumor-eradicating therapy in murine models indicates that a frequency of antigen-specific T cells of at least 1-10% of $CD8^+$ T cells may be employed with success. In human patients, this translates to a dose of about 2 to $20 \times 10^9$ cells, although higher and lower amounts of cells may be employed. It is noted that, in certain embodiments, the number of cells that is needed for therapeutic treatment using the methods and compositions of the present invention is generally less than disclosed in the prior art. For example, T-cells cultured by methods used in the art are generally at their terminal stage after prolonged ex vivo culture. Such cells display transient cytolytic effects against tumor cells and rapidly diminish in vivo following transfer. In contrast, the antigen-specific long lasting memory T cells generated using some culture system embodiments of the present invention have augmented stem cell-like property, i.e. enhanced ability to self-renew to persist accompanied by augmented capability to proliferate to become effector T cells upon the antigenic stimulation, both in vivo and in vitro. Upon re-encounter of the antigen, such cells can rapidly and vigorously proliferate to elaborate effector functions. Thus, the volume of cells that is needed for treatment of a human patient is generally significantly less than that of cells generated using conventional approaches taught by the prior art. For example, in some embodiments, the amount of tumor-reactive T cells applied to the patient can be reduced by 5 to 10 fold over prior art methods, e.g., $2 \times 10^8$ to $4 \times 10^9$. It is further noted that while repeated transplantation can improve the efficacy of T cell-mediated anti-tumor activity, embodiments of the present invention may employ one a single administration of the long-term memory T-cells. Such therapy may be sufficient for therapeutic treatment and may be further augmented by repeated antigen and cytokine therapy.

Types of Cancer

Methods of some embodiments of the present invention find use in the treatment of cancer and are not limited by the type of cancer. In some embodiments, methods may be directed towards treatment of solid tumors. Examples of solid tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Additional types of malignancies and related disorders include but are not limited to leukemia (acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia), polycythemia vera, lymphoma (Hodgkin's disease, non-Hodgkin's disease), multiple myeloma, Waldenström's macroglobulinemia, heavy chain disease, Solid tumors (sarcomas and carcinomas, fibrosarcoma, myxosarcoma, liposarcoma, chondrosarcoma, osteogenic sarcoma, chordoma angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma astrocytoma, medulloblastoma, craniopharyngioma, ependymoma, pinealoma, hemangioblastoma, acoustic neuroma, oligodendroglioma, meningioma, melanoma, neuroblastoma, retinoblastoma).

Co-Administration with Chemotherapeutic Agents

In some embodiments, adoptive cell immunotherapy may be conducted in combination with chemotherapy (e.g., Dudley et al., Semin. Oncol., 34:524-531, 2007; herein incorporated by reference in its entirety). Chemotherapy and adoptive cell transfer may be performed sequentially or simultaneously. For example, lymphodepleting chemotherapy may be conducted prior to adoptive cell transfer. The present invention is not limited by type of anti-cancer agent co-administered. Indeed, a variety of anti-cancer agents are contemplated to be useful in the present invention including, but not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

EXAMPLES

The following examples are provided in order to demonstrate and further illustrate certain preferred embodiments and aspects of the present invention and are not to be construed as limiting the scope thereof.

Example 1

Therapeutic Application of Memory CD8$^+$ T Cells for Adoptive Transfer

In the following example, patients in need of immunotherapy are treated by adoptive transfer of ex vivo-cultivated CD8$^+$ memory T cells.

Patients in need of adoptive transfer immunotherapy may have one or more diseases or conditions, including but not limited to cancer (e.g., renal cell carcinoma, melanoma, esophageal cancer, breast cancer, lung cancer, pancreatic cancer, or other malignancies), Alzheimer's disease, other amyloid disorders, sporadic inclusion-body myositis, intractable viral diseases, and other infectious diseases. Unprimed (naïve) CD8$^+$ T cells are obtained from peripheral blood of humans. In some instances, they may be taken from the patient; in other instances, they may be taken from another donor. Methods for isolation of CD8+ T cells are known in the art and include but are not limited to Magnetic Activated Cell Sorting (MACS) using commercially available kits containing immunomagentic beads (Miltenyi Biotec) (Busch et al., J. Immunol. Methods, 286:97-109, 2004; herein incorporated by reference in its entirety), or Fluorescence-Activated Cell Sorting (FACS) (Chen et al., PLoS Med., 2(10): e265, 2005; herein incorporated by reference in its entirety). In some instances, although methods of certain embodiments of the present invention were developed for augmenting the generation of precursors for long lasting tumor-reactive T cells from unprimed naïve T cells, they can be used for enhancing the generation of tumor-reactive memory T cells from either primed and antigen-experienced T cells, or both primed and unprimed memory T cells.

Figure 8:
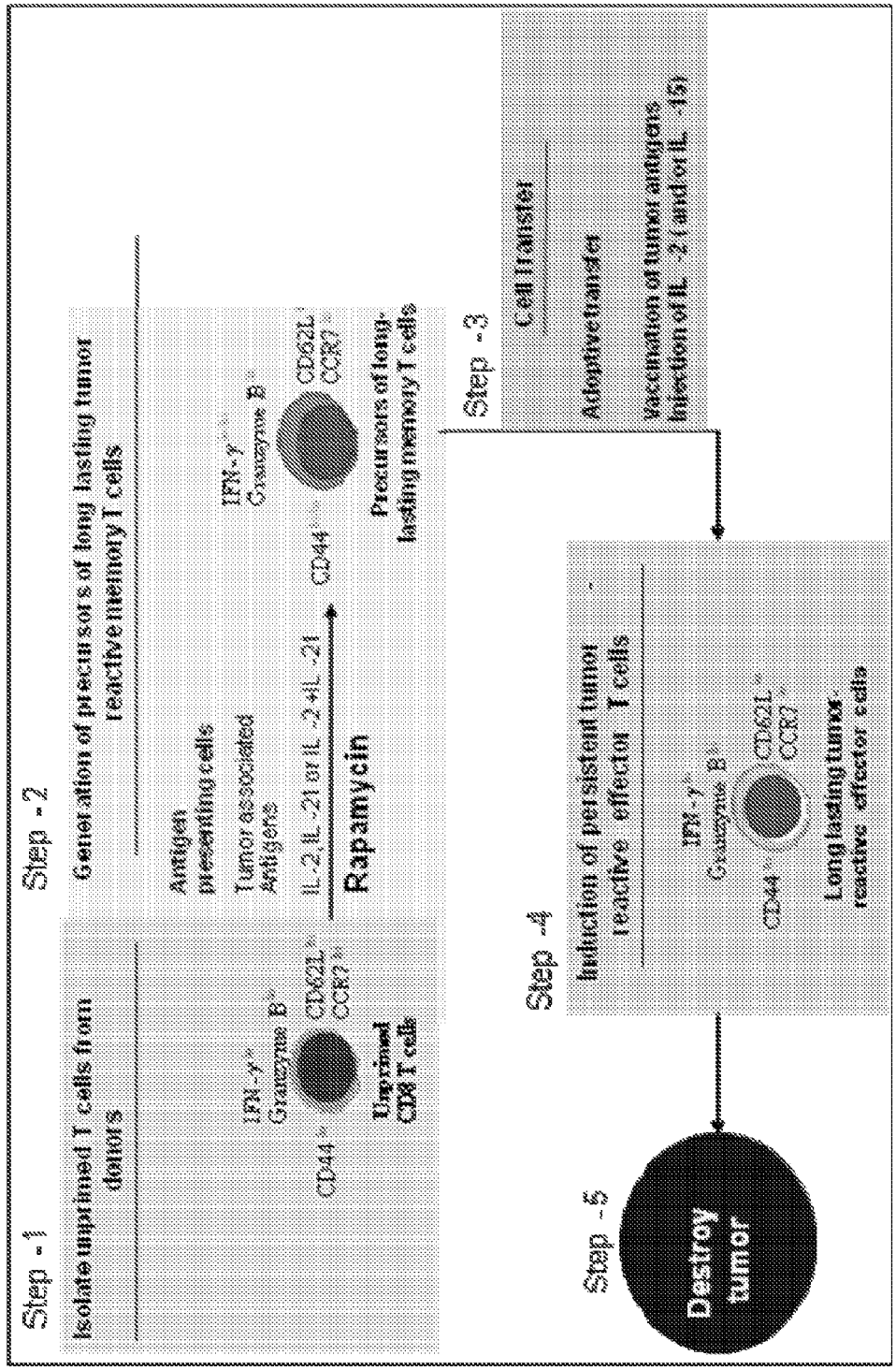
FIG. 8 shows one exemplary embodiment of an ex vivo culture method to generate the precursors of long-lasting memory T cells for T cell adoptive immunotherapy.
Figure 9:
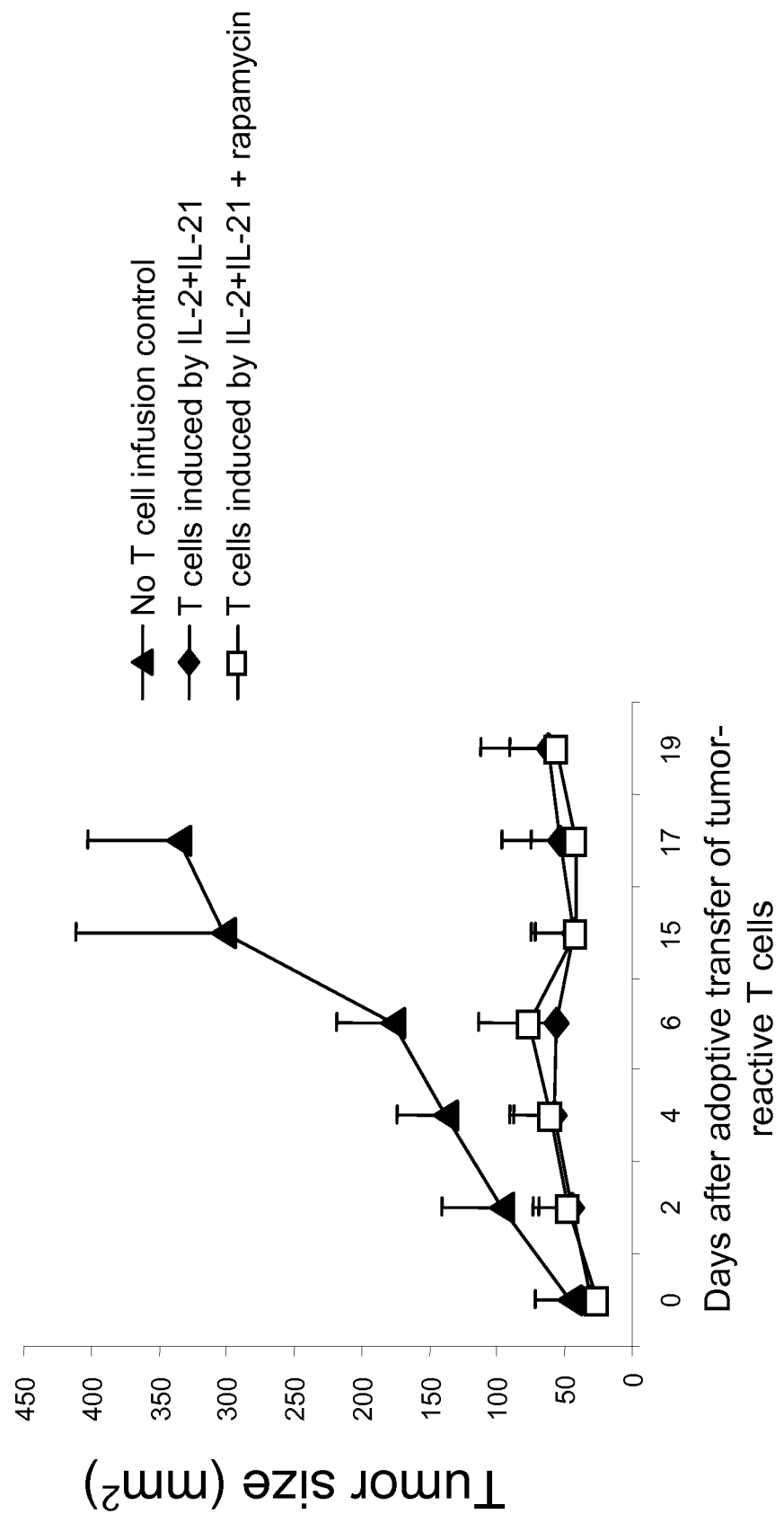
FIG. 9 shows adoptive transfer of in vitro generated long-lasting T memory precursor cells mediates melanoma regression in mice. Anti-tumor T cells were induced in the culture system described in the present application. Seven days after inoculation of mouse melanoma, these in vitro generated anti-tumor T cells were adoptively transferred into tumor bearing mice. The growth of tumor was monitored as indicated.

Following isolation of CD8+ T cells, the cells may be further processed to yield subsets of CD8+ T cells with desired characteristics. Methods for such isolation are known in the art and typically involve FACS (see, e.g., Example 3; Zhang et al., Nature Med., 111:1299-1305, 2005; herein incorporated by reference in its entirety). In some embodiments, for example, $CD44^{lo}CD8^+$ cells are isolated using FACS. In other embodiments, $IFN-\gamma^{lo}$ granzyme $B^{lo}$ $CD44^{lo}$ $CD62L^{hi}$ $CCR7^{hi}$ CD8+ T cells are isolated using FACS. Following isolation of desired subsets, cells are cultured ex vivo in the presence of antigen-presenting cells and/or antigens (e.g., tumor-associated antigens). One embodiment of an ex vivo culture scheme is shown in FIG. 8. While the present invention is not limited to any particular mechanism, and an understanding of the mechanism is not necessary to practice the present invention, antigen-presenting cells and antigens serve to activate the CD8+ T cells and thereby stimulate production of long-lasting memory T cells. Antigen-presenting cells may be dendritic cells, which can be obtained from cultured bone marrow cells and peripheral blood cells. In addition, other antigen-presenting cells, including but not limited to mitogen activated B lymphoblast cells, may be also used for activating unprimed T cells. In some embodiments, antigen-presenting cells used during ex vivo culture express high levels of co-stimulatory molecules including but not limited to CD86, CD40, and/or 4-1BBL. Tumor-associated antigens are known in the art and include but are not limited to anaplastic lymphoma kinase (ALK), ACRBP, BAGE, BCL-2, Tn218, carcino embryonic antigen (CEA), CD164, CD20, DNAJC2, EBAG9, ENOX2, ErbB 2, FATE1, FLT3-ITD, G250, GAGE1, Galectin 8, GPA33, GPNBB, HORMAD1, Her2, hTERT, IFITM2, LH39, LYK5, M2A oncofetal antigen, MAGE family antigens including but not limited to MAGE1, MAGE10, MAGE11, MAGE12, MAGEA2, MAGEA3, MAGEA4, MAGEA6, MAGEA8, MAGEA9, MAGEB18, MAGEB6, MABEC1, MAGED2, MAGEE1, MAGEH1, MAGEL2, MEL4, MelanA/MART1, melanoma associated antigen 100+, melanoma gp100, NRIP3, NYS48, OCIAD1, OFA-iLRP, OIP5, ovarian carcinoma-associated antigen (OV632), PAGE4, PARP9, PATE, plastin L, PRAME, prostate-specific antigen, proteinase 3, prostein, Reg3a, RHAMM, ROPN1, SART2, SDCCAG8, SEL1L, SEPT1, SLC45A2, SPANX, SSX5, STXGALNAC1, STEAP4, survivin, TBC1D2, TEM1, TRP1, tumor antigens of epithelial origin, XAGE1, XAGE2, and WT-1. For example, in clinic, the treating physician will determine the use of antigen based on the type of tumor and its related tumor-associated antigens. For example, in patients with melanoma, several melanoma associated antigenic peptides can be used for activating CD8+ T cells, including gp100 and MART1/MelanA. In patients with lymphoma, idiotype antigens and anaplastic lymphoma kinase (ALK) can be used for induce tumor-reactive T cells. —In patients with leukemia, BAGE, BCL-2, OFA-iLRP, FLT3-ITD, G250, hTERT, PRAME, proteinase 3, RHAMM, survivin, and WT-1 are all LAAs can be used as they have been shown to induce CD8 T cell response. In addition, antigens expressed by tumor stromal cells can also be used to activate T cells so that generated tumor-reactive T cells can attack the tumor environment (stromal cells) to eliminate the niche essential to the grow and survival of cancer cells. Antigens may also be included in the form of tumor cell lysates, proteins, and/or peptides. Antigens, vaccines, and/or peptides may be administered with suitable adjuvants. Examples of adjuvants include but are not limited to complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable. More than one antigen may be used for stimulation. In preferred embodiments, multiple rounds of stimulation are conducted. The number of rounds of stimulation may be 1, 2, 3, 4, 5, 6, 7, 8, . . . 20 or more.

Additionally, ex vivo culture may be conducted in the presence of other agents that promote cell growth and/or expansion of the CD8+ memory T cell population. In some embodiments, an inhibitor of mTOR is used during multiple rounds of antigenic stimulation. While the present invention is not limited to any particular mechanism, and an understanding of the mechanism is not necessary to practice the present invention, mTOR-inhibiting agents can preserve the stem cell-like property of antigen-activated T cells. Agents that inhibit mTOR include rapamyocin (sirolimus), CCI-779 (temsirolimus), everolimus (RAD-001), AP23573, rapamycin analogs (rapalogs), mTOR antibodies, mTOR siRNAs, agents inhibiting mTOR phosphorylation, agents inhibiting interaction of mTOR with its partners, amd agents inhibiting interaction of mTOR with its substrates. In some embodiments, rapamycin is used to inhibit mTOR. The amount of rapamycin used during ex vivo culture may be, for example, 0-2.5 nM, 2.5-5 nM, 5-10 nM, 10-20 nM, 20-30 nM, 30-50 nM, 50-100 nM, 100 nM-1 µM, 1-10 µM, 10 µM or more.

Additionally, in certain embodiments, ex vivo culture is conducted in the presence of cytokines. In some preferred embodiments, IL-2 is used. In some embodiments, IL-21 will be used. In some embodiments, both IL-2 and IL-21 are used. While the present invention is not limited to any particular mechanism, and an understanding of the mechanism is not necessary to practice the present invention, it is believed that IL-2 and/or IL-21 serve to further increase the frequency of tumor-reactive T cells that have great ability to generate long-lasting memory T cells to persist in vivo. While the present invention is not limited to any particular mechanism, and an understanding of the mechanism is not necessary to practice the present invention, it is believed that addition of IL-21 to the culture can further augment, in concert with rapamycin or other mTOR inhibitor, the stem cell-like activity of tumor-reactive T cells. In some embodiments, for multiple rounds of antigenic stimulation, a prolonged culture is necessary for increasing the frequency of tumor-reactive T cells and for generating sufficient number of tumor-reactive T cells for clinical application. Duration of each round of culture may be less than 1 day, 1-2 days, 2-3 days, 3-4 days, 4-5 days, 5-6 days, 6-7 days, 7 days or more.

One of skill in the art will appreciate that the volume of cells needed to treat a human patient may need to be tailored to the needs of each patient. Tumor-eradicating therapy in murine models indicates that a frequency of antigen-specific T cells of at least 1-10% of CD8$^+$ T cells may be used with success. In human patients, this translates to a dose of 2 to 20×10$^9$ cells. Higher and lower doses may be employed.

After administering cells to the patient by adoptive transfer, patients may receive further antigenic challenge. Such antigenic challenge may be presented by means known to one of skill in the art, e.g., vaccination with plasmid encoding tumor antigenic peptides and/or administration of antigen-presenting cells. Furthermore, the patient may further receive cytokine therapy. In some embodiments, IL-2 is administered to the patient. In some embodiments, IL-15 is administered to the patient. In some embodiment, both IL-2 and IL-15 are administered to the patient, either sequentially or simultaneously. In some embodiments, other cytokines are administered.

Memory T cell products of the ex vivo culture system may be analyzed prior to administration to a patient, or for other quality control purposes. In some embodiments, functional assays are performed to test the quality, identity, and/or functionality of the cells. In some embodiments, such assays may allow determination of cell phenotype based on at least one surface marker. Long lasting memory T cell precursors that are generated in some ex vivo culture system embodiments of the present invention express central memory like-phenotype ($CD44^{hi}CD62L^{hi}$) and memory stem cell-like phenotype ($CD44^{lo}CD62L^{hi}Sca-1^{hi}CD122^{hi}CD127^{hi}Bcl-2^{hi}$). Both of these T cell subsets are antigen-activated T cells, expressing high levels of CD122 but low levels of IFNγ. Phenotypically, they can be distinguished from short-lived antigen-activated T cells expressing the phenotype of $CD44^{hi}CD62L^{lo}$. Flow cytometry analysis can be used for measuring cell phenotype. In some embodiments, such assays may allow determination of expression patterns of genes relating to stem cell identity. Long-lasting memory T cells that are generated in some ex vivo culture systems of the present invention increase the expression of genes that are enriched in stem cells for stimulating the proliferation and self-renewal of stem cells, such as Ezh2, Hells, Bmi1, Survivin, p18$^{Ink4c}$ and p21. As compared to short-lived T cells generated from conventional cultures, increased expression of these genes indicates the generation of long-lasting memory T cells. Real-time PCR can be used for measuring the gene expression. Such testing for gene expression patterns may be performed with the aid of a kit designed for this purpose. In some embodiments, such assays may allow determination of cell function based on the ability to respond to antigenic stimulation. Repeated antigenic stimulation can be used for assessing whether memory T cell precursors generated in ex vivo cultures are able to persist in vivo after adoptive transfer. The specific antigen peptides and antigen-presenting cells will be added every 5 days into the culture containing memory T cell precursors. After 3 rounds of antigenic stimulation, cells may be recovered from the culture to measure: i) numbers of live cells; ii) number of cells producing IFN-γ; and iii) number of cells with cytolytic effect against the cognate tumor cells.

Cells may be administered to the patient by cell infiltration. Hematologic parameters may be monitored at regular intervals by obtaining complete and differential blood counts. After administering adoptive transfer immunotherapy to the patient, the patient may be assessed for the degree to which the therapy was effective. In some embodiments, the efficiency of adoptive transfer may be assessed by analyzing the regression of tumor. Clinical and radiographic responses (e.g. MRI and CT) can be used for monitoring the effector tumor-reactive T cells on tumor growth. Alternatively or in addition, clinical or histological images may be used to monitor tumor growth. In some embodiments wherein tumor cells are fluorescently labeled or made to be visualizable by detection of fluorescence, bioluminescent in vivo imaging may be used for monitoring tumor growth. In some embodiments, the efficiency of adoptive transfer may be assessed by analyzing the persistence of functional tumor-reactive T cells. This may involve determining i) the frequency of infused tumor-reactive T cells, for example using an antigen peptide/MHC-I tetramer technique and intracellular staining and ELISPOT assay of IFN-γ producing cells to test the frequency and persistence of tumor-reactive T cells; ii), the recall response of infused tumor-reactive T cells, for example by conducting ex vivo culture in the presence of antigen-presenting cells pulsed with antigen peptides to examine the ability of infused tumor-reactive T cells to respond to the restimulation of the specific antigen. This latter method is used to measure the proliferation, effector differentiation and survival of recovered tumor-reactive T cells upon the antigenic restimulation.

Example 2

Enhancing Oxidative Phosphorylation by Rapamycin in CD8+ T Cells During Antigenic Priming Augments their Generation of Long-Lived Memory T Cells In this example, it was demonstrate that antigen-activated CD8+ T cells treated with rapamycin in vitro during the priming phase demonstrate significantly augmented ability to become long-lived memory T cells in vivo. It was found that rapamycin-treated CD8+ T cells expressed memory precursor phenotypes, with high levels of CD62L and CD127 but low levels of KLRG-1, PD-1 and IFN-y. These cells markedly increased mitochondrial oxidative phosphorylation and had obtained greater ability to survive upon growth factor withdrawal as compared to untreated control cells Inhibition of mitochondrial oxidative phosphorylation by oligomycin drastically reduced the ability to rapamycin-treated CD8+ T cells to resist to growth factor withdrawal. Furthermore, these rapamycin-treated CD8+ T cells generated significantly more memory T cells over a period of 6 months than control cells. These long-lived memory T cells had potent ability to produce IFN-y and proliferate when reexposed to the specific antigen both in vivo and in vitro. These data indicate that rapamycin regulates cell metabolism in a context dependent manner, and augmentation of oxidative phosphorylation in proliferating T cells by rapamycin in vitro during antigenic priming drastically increases the pool size of memory precursors that can become long-lived memory T cells in vivo. These findings have significant implications in optimizing T cell properties to improve the efficacy of adoptive immunotherapy.

Results

Rapamycin Induces In Vitro Antigen-Primed CD8+ T Cells with Features of Long-Lived Memory Precursor Cells.

To determine whether rapamycin can induce long-lived CD8+ T memory precursors in vitro during antigenic-priming phase, CFSE-labeled CD44loCD8+ naïve T cells (naive T) were labeled in the presence of DCs, LCMV gp33 (10-7M), IL-2 and different concentrations of rapamycin (ranging from 0 to 100 nM). Stimulation of CD8+ naive T with gp33 induced their vigorous division and expansion (FIGS. 1A and B). Addition of rapamycin did not impair either cell division or expansion of gp33 (10-7M)-activated CD8+ T cells over a period of 8 days, with minimal increased number of proliferating CD8+ T cells in the presence of 5 to 50 nM rapamycin (FIGS. 1A and B). Interestingly, there were significantly more antigen-activated CD8+ T cells undergoing apoptotic death in the cultures without rapamycin (named IL-2 CD8+ T cells) as compared to cells cultured in the presence of rapamycin (named Rapa CD8+ T cells). IL-2 CD8+ T cells had more than 35% dead cells at day 8 after culture, whereas Rapa CD8+ T cells derived from the culture with 50 or 100 nM rapamycin contained less than 5% dead cells (FIG. 1A, lower panel). Most importantly, Rapa CD8+ T cells retained greater ability than IL-2 cells to survive even over a period of 84 hours even after removal of rapamycin from the culture (FIG. 1C). This effect was associated with the strength of antigenic stimulation, as that rapamycin only increased the viability of CD8+ T cells in the cultures with gp33 at a concentration higher than 10-8 M (FIG. 1D).

Figure 2:
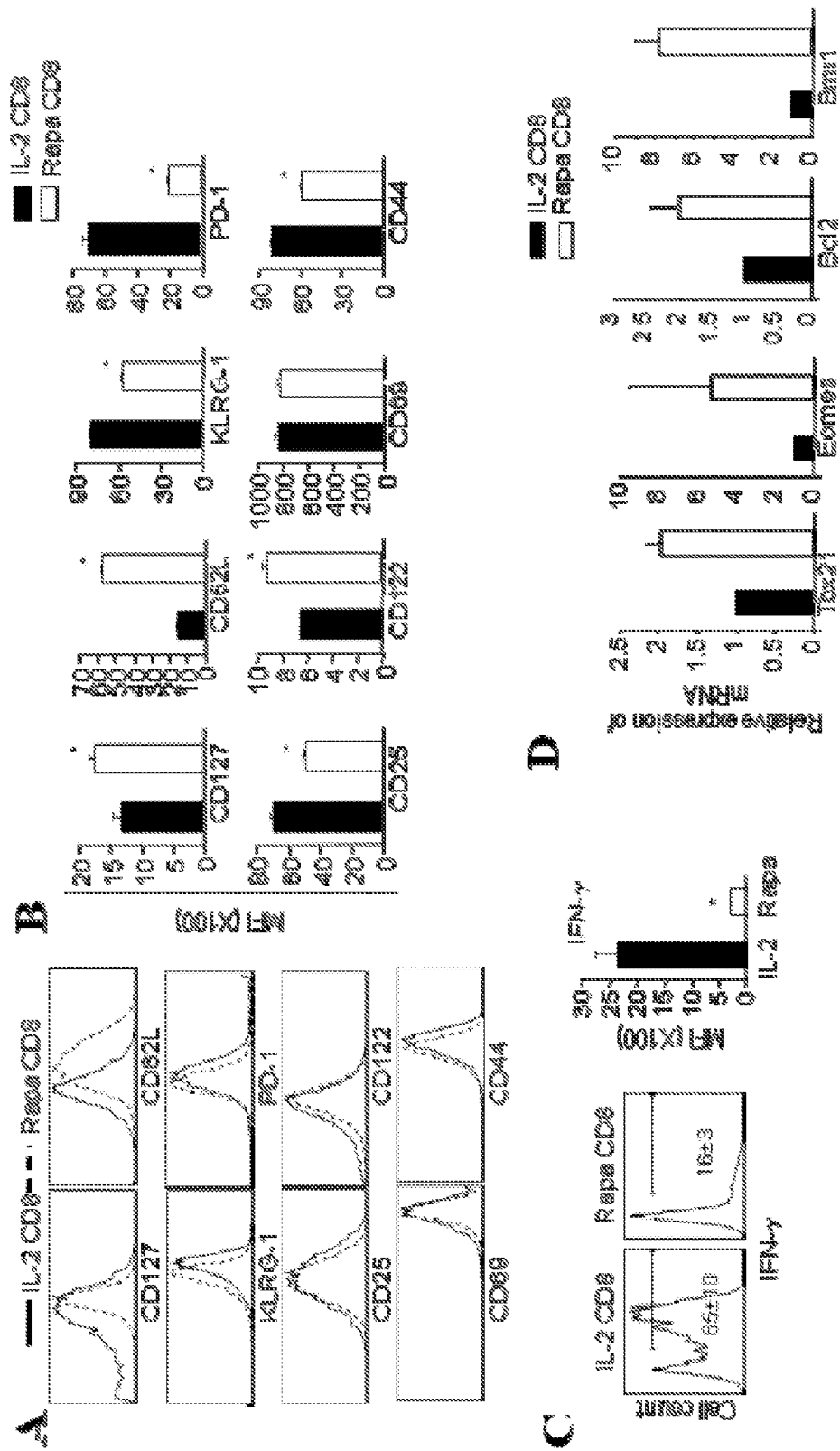
FIG. 2 shows rapamycin induces the generation of memory precursor cells. (A and B) Flow cytometry of P14 CD8+ T cells after priming with B6-derived DCs pulsed with gp33 and IL-2 with or without 50 nM rapamycin (named IL-2 CD8+ T cells and Rapa CD8+ T cells, respectively) (A), and the mean fluorescence intensity (MFI) was calculated (B). (B) Flow cytometry and MFI enumeration of the expression of IFN-γ in IL-2 cells and Rapa cells after stimulated with anti-CD3 antibody overnight. (D) Quantitative RT-PCR analysis of the expression of Tbx21, Eomes, Bcl-2 and Bmi-1 in IL-2 CD8+ T cells and Rapa CD8+ T cells. Data are shown as means±SD and representative from two independently performed experiments. *p<0.05.

Flow cytometry analysis showed that proliferating Rapa CD8+ T cells expressed higher levels of CD62L (CD62Lhi) and CD127 (CD127hi) but lower levels of KLRG1 (KLRG1lo) and PD-1 (PD-1lo) than IL-2 CD8+ T cells (FIGS. 2A and B), a phenotype of long-lived CD8+ T memory precursor cells. Notably, whereas most IL-2 cells (up to 75%) produced high levels of IFN-$\gamma$, Rapa CD8+ T cells only produced minimal IFN-$\gamma$ (FIG. 2C). This reduced IFN-$\gamma$ production in Rapa CD8+ T cells was not associated with repressed expression of transcription factors required for effector differentiation. As shown in FIG. 2D, relative to IL-2 CD8+ T cells, Rapa CD8+ increased expression of Eomesodermin (Eomes) and Tbx21 (encoding T-bet), two transcription factors essential to effector T cell development. Taken together, all these results indicates that rapamycin induces the generation of proliferating CD8+ T cells with the features of long-lived memory precursors T cells.

Rapamycin Increases the Oxidative Phosphorylation in Antigen-Primed CD8+ T and their Ability to Resist IL-2 Withdrawal.

Figure 3:
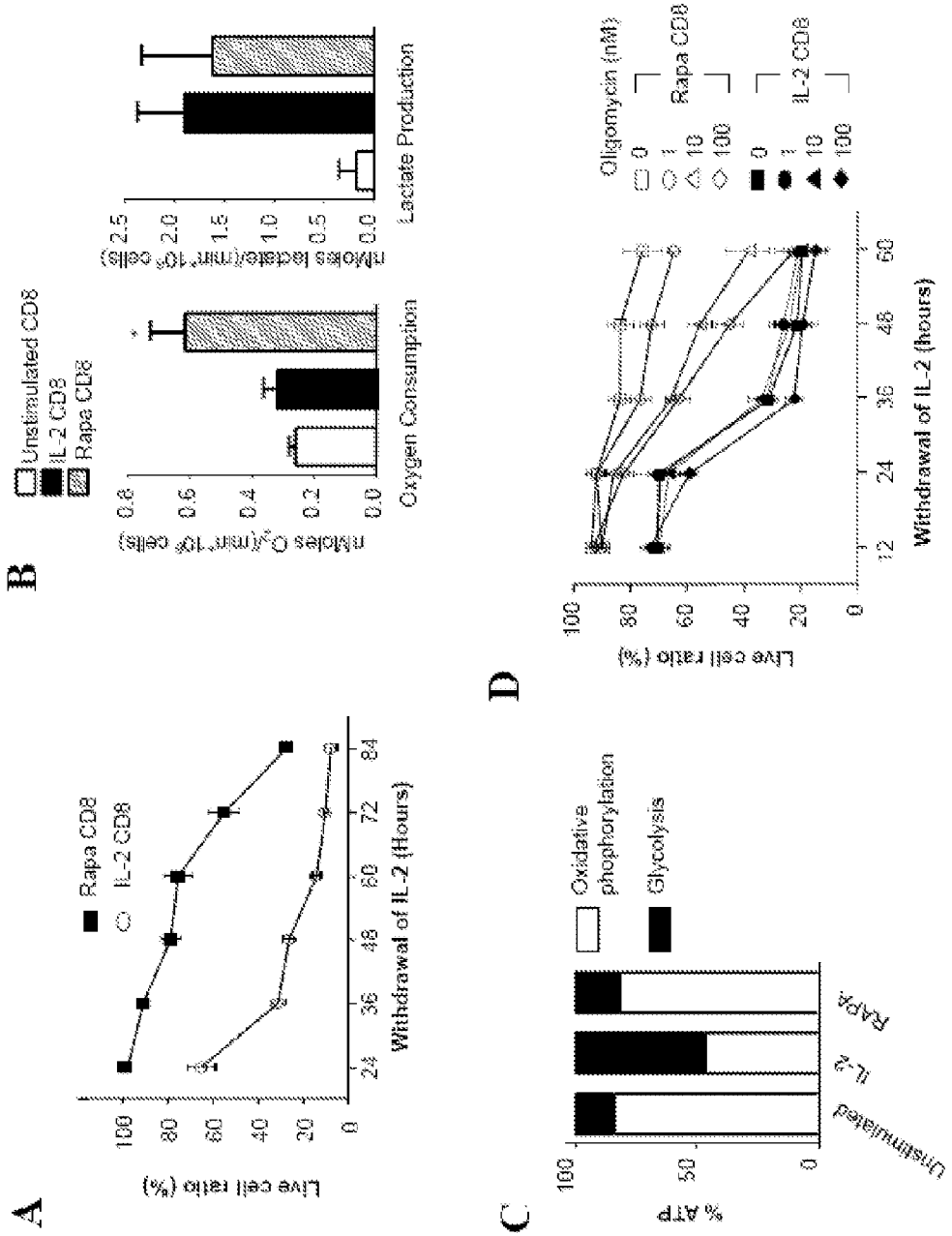
FIG. 3 rapamycin increases the oxidative phosphorylation in antigen-primed CD8+ naive T and their ability to resist IL-2 withdrawal in vitro. IL-2 CD8+ cells and Rapa CD8+ cells were collected 6 days after in vitro culture and washed twice. (A) IL-2 CD8+ cells and Rapa CD8+ cells were washed thrice and further cultured in the absence of IL-2. Graphs show live cell ratios at different time point after secondary culture. (B) Oxygen consumption and lactate production assay were performed as described in material and methods. Freshly isolated naïve CD8+ T cells were used as control. Data are represented as means±SD. (C) The ratios of oxidative phosphorylation and glycolysis contributed to the total ATP generation were calculated. (D) IL-2 CD8+ cells and Rapa CD8+ cells were washed thrice and further cultured in the absence of IL-2, with or without addition of different doses of oligomyxin. Live cell ratio was calculated at different time point. Data are represented as means±SD. Results are representative of two independently performed experiments. *p<0.05.

It has been suggested that effector T cells may cease proliferating and undergo apoptotic contraction when growth factors and antigenic stimulation diminish during apoptotic contraction. Effector T cells capable of resisting to growth factor withdrawal have the ability to survive and to become memory T cells. It was next determined whether Rapa CD8+ T cells had obtained the ability to resist growth factor withdrawal. Both Rapa CD8+ T cells and IL-2 CD8+ T cells were recovered from the primary culture, washed three times to completely remove IL-2, and transferred into the secondary culture in the absence of IL-2. It was found that IL-2 CD8+ T cells rapidly diminished to 40% in cultures by 24 hours after IL-2 withdrawal and further reduced to less than 10% by 72 hours (FIG. 3A). In contrast, Rapa CD8+ T cells had greater ability than IL-2 cells to resist IL-2 withdrawal. Approximately 100% of Rapa CD8+ T cells were viable by 24 hours after IL-2 withdrawal, with more than 60% of them remaining lived by 74 hours after withdrawal (FIG. 3A). These results indicate that rapamycin-treatment endows proliferating CD8+ T cells the ability to resist IL-2 withdrawal.

Data from recent studies indicate that augmented oxidative phosphorylation is critical to the generation of memory T cells from effector T cells that have enhanced ability to resist against IL-2 withdrawal. The effect of rapamycin on oxidative phosphorylation was assessed in proliferating CD8+ T cells. It was found that both IL-2 CD8+ T cells and Rapa CD8+ T cells equally increased production of lactate relative to unstimulated CD8 naive T. In contrast, Rapa CD8+ T cells increased oxygen consumption 2-fold more than IL-2 CD8+ T cells (FIG. 3B). Consequently, Rapa CD8+ T cells had more than 90% of ATP derived from oxidative phosphorylation metabolism, whereas IL-2 CD8+ T cells used glycolysis metabolism to supply 60% of ATP (FIG. 3C). Thus, upon rapamycin treatment, antigen-primed CD8+ T cells enhance the energy supplement from oxidative phosphorylation of mitochondrion despite their preservation of glycolytic energy supplement. This was further confirmed by addition of the oxidative phosphorylation-inhibitor oligomycin. Upon IL-2 withdrawal, oligomycin dose-dependently reduced the ability of Rapa CD8+ T cells to resist IL-2 withdrawal (FIG. 3D). Thus, augmented oxidative phosphorylation in mitochondrion of Rapa CD8+ T cells may account for their improved viability in vitro.

Rapa CD8+ T Cells have Superior Ability to IL-2 CD8+ T Cells to Survive In Vivo.

Figure 4:
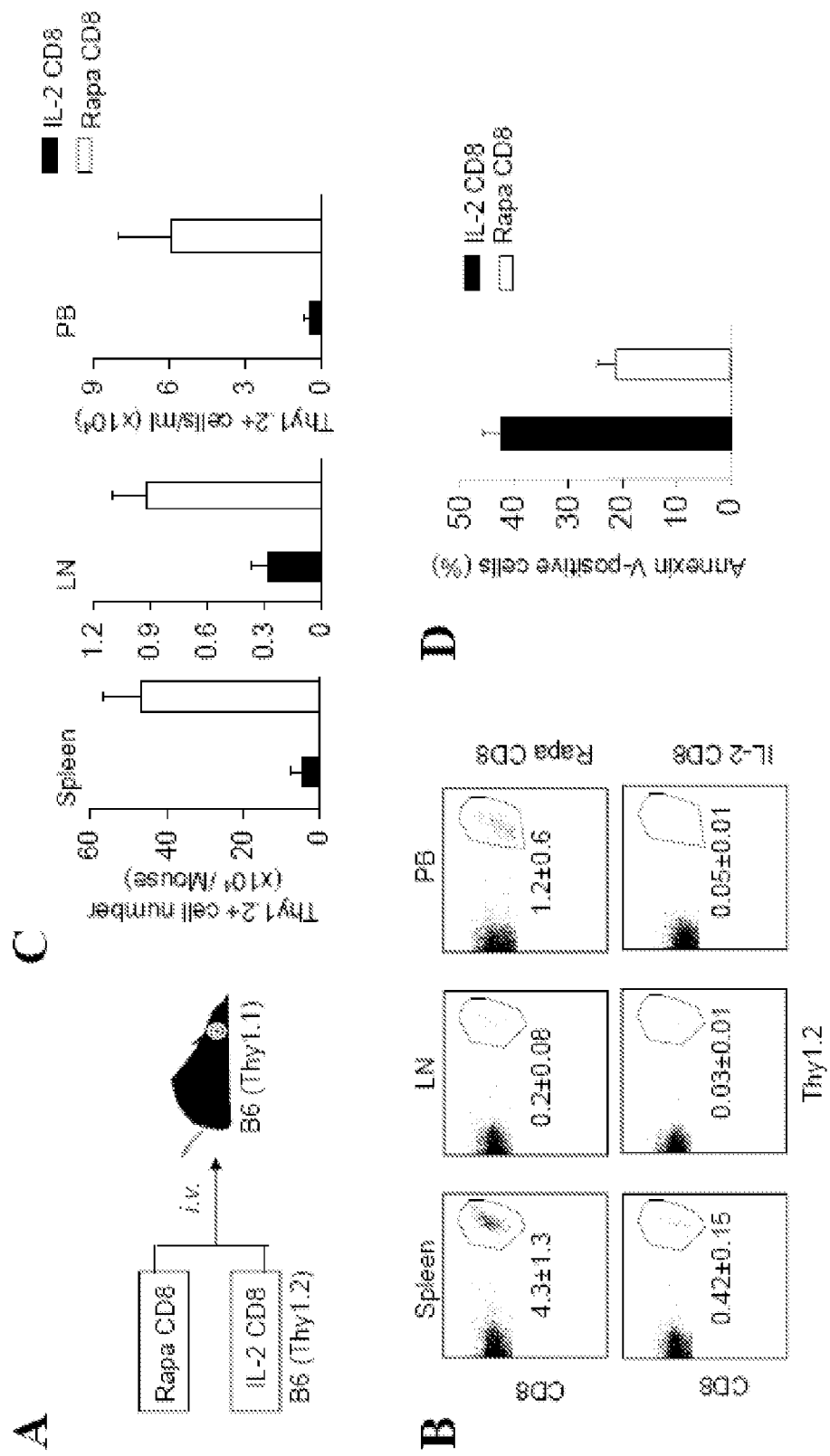
FIG. 4 shows rapamycin increases the survival capacity of antigen-primed CD8+ naive T in nonlymphopenic recipient mice. IL-2 CD8+ cells and Rapa CD8+ cells were collected 6 days after in vitro culture. (A) Two million of those cultured T cells were transferred into normal Thy1.1 mice separately, and mononuclear cells from spleen, lymph nodes and peripheral blood were isolated one day after the adoptive transfer. (B) Flow cytometry analysis for the expression of CD8 and Thy1.2. Dot plots show the fraction of CD8+ Thy1.2+P14 T cells. (C) Graphs demonstrate the absolute numbers of the adoptively transferred CD8+ Thy1.2+ lymphocytes in the spleen, lymph nodes and peripheral blood. (D) Gated CD8+ Thy1.2+P14 T cells were analyzed by Annexin V staining Graphs show the percentage of Annexin V-positive CD8+ Thy1.2+P14 T cells in each group. All data are shown as means±SD and representative of two independently performed experiments. *$p<0.05$.

It was next assessed whether Rapa CD8+ T cells with augmented capability of resistance to IL-2 withdrawal have improved ability to survive in vivo following their adoptive transfer. To test this hypothesis, Rapa CD8+ and IL-2 CD8+ T cells (Thy1.2) were adoptively transferred into normal syngenic Thy1.1+C57B/6 (B6) mice (FIG. 4A). Without inducing lymphopenia in these recipient mice, there are limited amount of T cell growth factors available to infused T cells, such as IL-2, IL-7, and IL-15. It was found that IL-2 CD8+ T cells were minimally detected in the peripheral blood (PB), lymph node (LN) and spleen by 24 hours after transfer (FIGS. 4B and C). In contrast, Rapa CD8+ T cells were readily detected in recipients, with approximate 10-fold more Rapa CD8+ T cells being recovered from the spleen and PB as compared to IL-2 CD8+ T cells (FIGS. 4B and C). These results suggest that IL-2 CD8+ T cells rapidly diminish in vivo in normal mice with limited available T cell growth factors.

Figure 5:
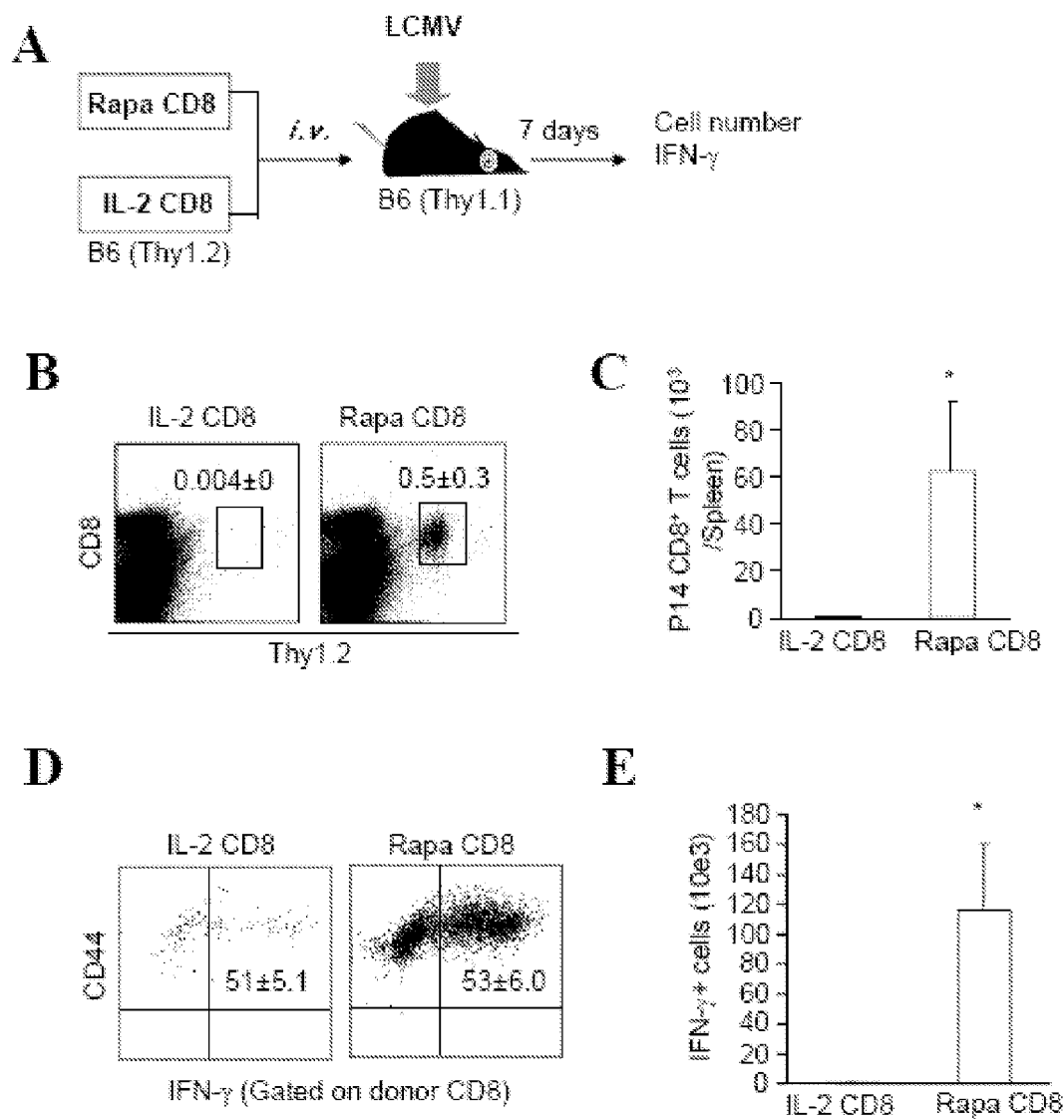
FIG. 5. Rapamycin induces antigen-primed CD8+ naive T with the ability to respond to LCMV infection in vivo. (A) Normal Thy1.1+B6 mice received IL-2 CD8+ cells and Rapa CD8+ cells ($2\times10^6$ cells/mouse), followed by LCMV ($5\times10^5$ PFU) infection. Seven days after transfer, splenic cells were collected from those recipient mice. (B) Flow cytometry analysis was performed. Dot plots show the fraction of CD8+ Thy1.2+P14 T cells. (C) Graphs demonstrate the absolute numbers in the spleens of mice receiving IL-2 CD8+ T cells and mice receiving Rapa CD8+ T cells. (D and E) Splenic cells isolated from recipient mice receiving IL-2 CD8+ cells or Rapa CD8+ cells were restimulated in vitro with gp33 ($10^{-6}$ M) for 5 hours for measuring the production of IFN-γ. Flow cytometry analysis shows the percentage of IFN-γ-producing CD8+ T cells (D). Graphs demonstrate the absolute number CD8+ Thy1.2+P14 T cells producing IFN-γ (E). All data are shown as means±SD and representative of three independently performed experiments. *$p<0.05$.

Previous studies have demonstrated that antigenic stimulation plays an important role in regulating activated T cell survival in vivo. It is possible that in these normal Thy1.1 B6 mice, rapid diminishment of IL-2 CD8+ T cells in vivo could be accounted for by deprivation of the specific antigen. To test this hypothesis, Thy1.1 B6 recipients were infected with lymphocytic choriomenigitis (LCMV) immediately following adoptive transfer of Rapa CD8+ T cells and IL-2 CD8+ T cells. Seven days after transfer, donor-derived T cells were recovered from the spleens of these recipient mice. Adoptively transferred CD8+ T cells were hardly detected in the spleens of mice receiving IL-2 CD8+ T cells (0.004%) (FIG. 5A). In contrast, about 125-fold more transferred CD8+ T cells were recovered in the spleens of mice receiving Rapa CD8 T cells than that in mice receiving IL-2 CD8+ T cells (FIG. 5A). Furthermore, most effector T cells derived from Rapa CD8+ T cells produced highly levels of IFN-$\gamma$, with 100-folds more IFN-$\gamma$ producing cells in the recipient mice receiving Rapa CD8+ T cells as compared to IL-2 CD8+ T cell recipients (FIG. 5B). Thus, antigenic stimulation can not rescue IL-2 CD8+ T cells in vivo. These data suggest that Rapa CD8+ T cells have superior ability to IL-2 CD8+ T cells to survive and to respond to LCMV infection in vivo.

Rapa CD8+ T Cells Develop into Long-Lived Memory T Cells In Vivo.

Figure 6:
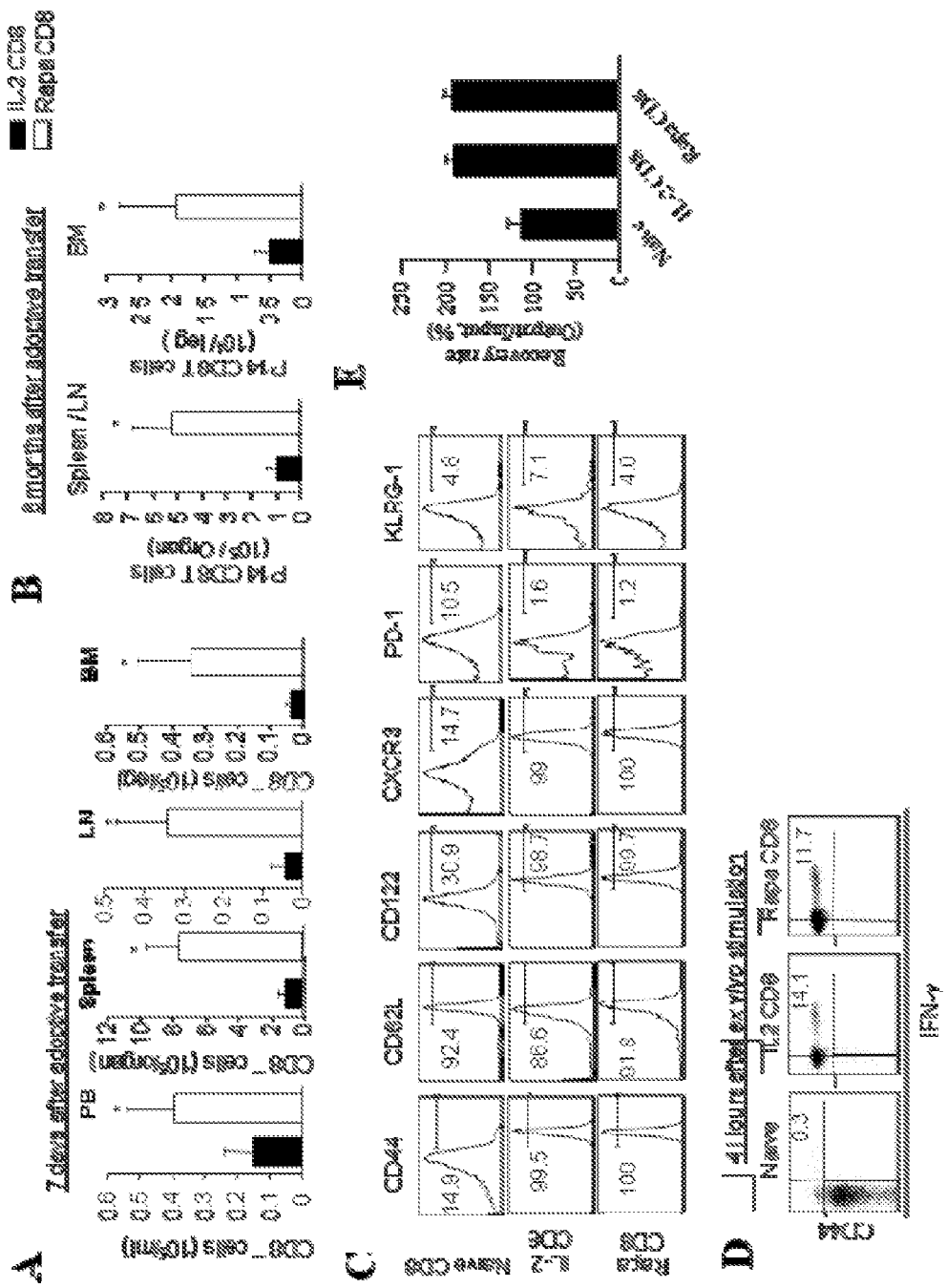
FIG. 6 shows antigen-primed CD8+ T cells in the presence of rapamycin have great ability to persiste long-time in vivo. Sublethally irradiated Thy1.1 mice were administered with two million of those cultured IL-2 CD8+ cells and Rapa CD8+ T cells respectively. Seven days (A) and 6 months (B) after the transfer, flow cytometry analysis were performed and the absolute numbers of the adoptively transferred CD8+ Thy1.2+ lymphocytes were enumerated in peripheral blood, spleen, lymph nodes and bone marrow. Graphs show the number of transferred P14 CD8+ T cells. (C) Histograms show the expression of surface markers in P14 CD8+ T cells recovered at 6 months after transfer from recipients of Rapa CD8+ T cells and recipients of IL-2 P14 CD8+ T cells, respectively. (D) Recovered P14 CD8+ T cells were stimulated with anti-CD3 Ab (2.5 ug/ml) for 4 hours and analyzed for their production of IFN-γ. P14 CD8+ naïve T cells derived from normal P14 mice were cultured as control. Dot plots show the fraction of IFN-γ producing cells. (E) These P14 CD8+ Thy1.2+ cells ($4\times10^4$) recovered at 6 months from recipients were cultured with B6 DCs pulsed with gp33 ($10^{-13}$ M) for another 4 days. Cells were collected from the cultures and counted. Graphs show the number of cells. Data are shown as means±SD and representative of two independently performed experiments. *$p<0.05$.

It was determined whether Rapa CD8+ T cells are able to develop into long-lasting memory T cells in vivo. Rapa CD8+ T cells (Thy1.2+) were adoptively transferred into sub-lethally irradiated Thy1.1 mice followed by vaccination with gp33-pulsed DCs at the day of transfer. IL-2 CD8+ T cells were transferred as controls. Sublethal irradiation creates lymphopenic environment capable of inducing T cell homeostatic proliferation in vivo. Six months later, donor CD8+ T cells were recovered from the PB, spleen, LN and bone marrow (BM) of these recipients. Interestingly, IL-2 CD8+ T cells were clearly detected in these irradiated recipient mice 7 days and 6 months after adoptive transfer (FIGS. 6A and B). This suggests that homeostatic factors (e.g., self-peptide and T cell growth factors) are essential to IL-2 CD8+ T cell survival and persistence. As compared to IL-2 CD8+ T cells, Rapa CD8+ T cells gave rise to approximate 5-fold more donor CD8+ T cells both at day 7 and 6 months after adoptive transfer (FIGS. 6A and B). Relative to CD8+ naive T, surviving CD8+ T cells derived from either Rapa CD8+ T cells or IL-2 CD8+ T cells expressed high levels of CD44, CD62L, CD122 and CXCR3 (FIG. 6C), a typical phenotype of long-lived memory T cells. Intracellular cytokine assay showed that both Rapa CD8+ T cell- and IL-2 CD8+ T cell-derived cells had the ability to rapidly produce high levels of IFN-γ upon short-term stimulation with anti-CD3 Ab (FIG. 6D), and retained the capability to proliferate in vitro when restimulated with gp33 peptide-pulsed DCs (FIG. 6E). Thus, as compared to IL-2 CD8+ T cells Rapa CD8+ T cells generate significantly more long-lived memory T cells that can persist over a period of 6 months in vivo. This difference in the ability to generate long-lasting memory T cells can be detected as early as 7 days after adoptive transfer. However, at the single cell level, memory T cells derived from either Rapa CD8+ T cells or IL-2 CD8+ T cells express the same memory phenotype and retain a similar ability to respond to antigenic-restimulation in vitro.

Figure 7:
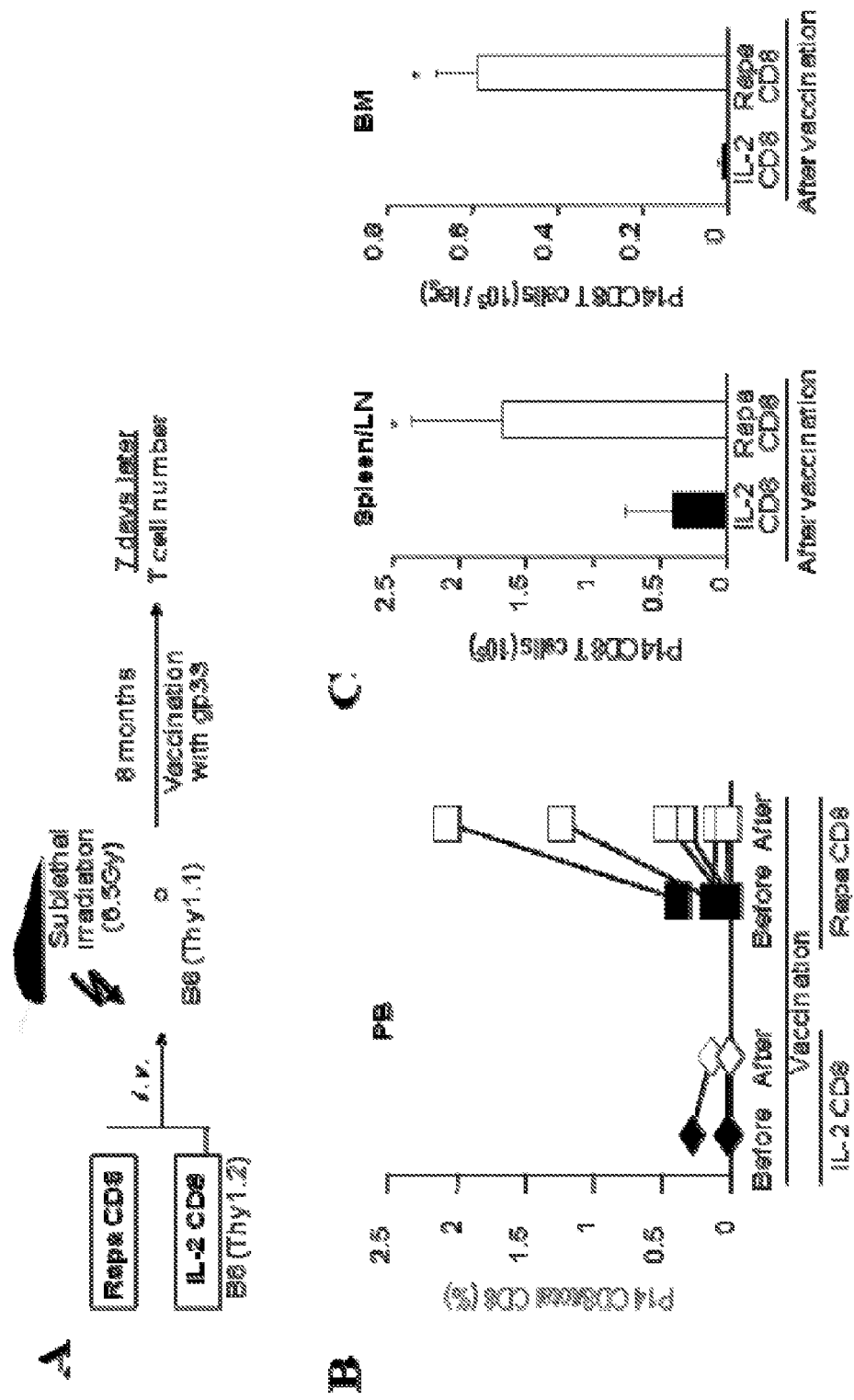
FIG. 7 shows rapamycin-induced long-lived CD8+ T cells can respond to the restimulation in vivo. (A) Eight months after adoptive transfer of IL-2 CD8+ cells (n=5) or Rapa CD8+ cells (n=6), recipient mice were rechallenged gp33 emulsified in CFA. Seven days later, transferred T cells were recovered from PB, Spleen and LN, and BM, stained for flow cytomery analysis. (B) Percentage of transferred P14 CD8+ T cells (Thy1.2+) in peripheral blood before and after immunization. (C) Absolute numbers of transferred P14 CD8+ T cells in the spleen/LN and bone marrow (BM) after immunization. Data are shown as means±SD. *$p<0.05$.

It was further tested whether these memory T cells are able to respond in vivo to vaccination, mice were immunized at 8 months after adoptive transfer of these mice with gp33 emulsified in CFA (FIG. 7A). Seven days later, flow cytometry analysis was used to measure the number of donor CD8+ T cells in the PB, spleen, LN and BM. It was found that vaccination increased the fraction of P14 CD8+ T cells in the PB of mice receiving Rapa CD8+ T cells (n=6), but not that of mice receiving IL-2 CD8+ T cells (FIG. 7B). This suggested that Rapa CD8+ T cells retained greater ability than IL-2 CD8+ cells to respond to vaccination in vivo 8 months after adoptive transfer. Furthermore, as compared to IL-2 CD8+ T cell recipients, mice receiving Rapa CD8+ T cells contained were 3-fold more donor CD8+ T cells in the spleen/LN and 10-fold more in BM, respectively (FIG. 7C). These data indicate that memory T cells derived from Rapa CD8+ T cells also function in vivo in response to secondary challenge.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

All of which are Herein Incorporated by Reference

1. Ahmed, R., and D. Gray. 1996. Immunological memory and protective immunity: understanding their relation. Science 272:54-60.
2. Fearon, D. T., P. Manders, and S. D. Wagner. 2001. Arrested differentiation, the self-renewing memory lymphocyte, and vaccination. Science 293:248-250.
3. Lanzavecchia, A., and F. Sallusto. 2002. Progressive differentiation and selection of the fittest in the immune response. Nat Rev Immunol 2:982-987.
4. Wherry, E. J., and R. Ahmed. 2004. Memory CD8 T-cell differentiation during viral infection. J Virol 78:5535-5545.
5. Masopust, D., S. M. Kaech, E. J. Wherry, and R. Ahmed. 2004. The role of programming in memory T-cell development. Curr Opin Immunol 16:217-225.
6. Bevan, M. J. 2004. Helping the CD8(+) T-cell response. Nat Rev Immunol 4:595-602.
7. Lanzavecchia, A., and F. Sallusto. 2005. Understanding the generation and function of memory T cell subsets. Curr Opin Immunol 17:326-332.
8. Badovinac, V. P., and J. T. Harty. 2006. Programming, demarcating, and manipulating CD8+ T-cell memory. Immunol Rev 211:67-80.
9. Williams, M. A., B. J. Holmes, J. C. Sun, and M. J. Bevan. 2006. Developing and maintaining protective CD8+ memory T cells. Immunol Rev 211:146-153.
10. Hinrichs, C. S., L. Gattinoni, and N. P. Restifo. 2006. Programming CD8+ T cells for effective immunotherapy. Curr Opin Immunol 18:363-370.
11. Gattinoni, L., D. J. Powell, Jr., S. A. Rosenberg, and N. P. Restifo. 2006. Adoptive immunotherapy for cancer: building on success. Nat Rev Immunol 6:383-393.
12. June, C. H. 2007. Principles of adoptive T cell cancer therapy. J Clin Invest 117:1204-1212.
13. Wakim, L. M., J. Waithman, N. van Rooijen, W. R. Heath, and F. R. Carbone. 2008. Dendritic cell-induced memory T cell activation in nonlymphoid tissues. Science 319:198-202.
14. Joshi, N. S., and S. M. Kaech. 2008. Effector CD8 T cell development: a balancing act between memory cell potential and terminal differentiation. J Immunol 180:1309-1315.
15. Hinrichs, C. S., R. Spolski, C. M. Paulos, L. Gattinoni, K. W. Kerstann, D. C. Palmer, C. A. Klebanoff, S. A. Rosenberg, W. J. Leonard, and N. P. Restifo. 2008. IL-2 and IL-21 confer opposing differentiation programs to CD8+ T cells for adoptive immunotherapy. Blood 111:5326-5333.
16. Schmitt, T. M., G. B. Ragnarsson, and P. D. Greenberg. 2009. T Cell Receptor Gene Therapy for Cancer. Hum Gene Ther.
17. Rosenberg, S. A. 2004. Shedding light on immunotherapy for cancer. N Engl J Med 350:1461-1463.
18. Kaech, S. M., S. Hemby, E. Kersh, and R. Ahmed. 2002. Molecular and functional profiling of memory CD8 T cell differentiation. Cell 111:837-851.
19. Bannard, O., M. Kraman, and D. T. Fearon. 2009. Secondary replicative function of CD8+ T cells that had developed an effector phenotype. Science 323:505-509.
20. Prlic, M., and M. J. Bevan. 2008. Exploring regulatory mechanisms of CD8+ T cell contraction. Proc Natl Acad Sci USA 105:16689-16694.
21. Kaech, S. M., E. J. Wherry, and R. Ahmed. 2002. Effector and memory T-cell differentiation: implications for vaccine development. Nat Rev Immunol 2:251-262.
22. Wherry, E. J., V. Teichgraber, T. C. Becker, D. Masopust, S. M. Kaech, R. Antia, U. H. von Andrian, and R. Ahmed. 2003. Lineage relationship and protective immunity of memory CD8 T cell subsets. Nat Immunol 4:225-234.
23. Kallies, A. 2008. Distinct regulation of effector and memory T-cell differentiation. Immunol Cell Biol 86:325-332.

24. Pearce, E. L., M. C. Walsh, P. J. Cejas, G. M. Harms, H. Shen, L. S. Wang, R. G. Jones, and Y. Choi. 2009. Enhancing CD8 T-cell memory by modulating fatty acid metabolism. Nature 460:103-107.
25. Wherry, E. J., D. L. Barber, S. M. Kaech, J. N. Blattman, and R. Ahmed. 2004. Antigen-independent memory CD8 T cells do not develop during chronic viral infection. Proc Natl Acad Sci USA 101:16004-16009.
26. Bhaskar, P. T., and N. Hay. 2007. The two TORCs and Akt. Dev Cell 12:487-502.
27. Wullschleger, S., R. Loewith, and M. N. Hall. 2006. TOR signaling in growth and metabolism. Cell 124:471-484.
28. Thomson, A. W., H. R. Turnquist, and G. Raimondi. 2009. Immunoregulatory functions of mTOR inhibition. Nat Rev Immunol 9:324-337.
29. Schieke, S. M., D. Phillips, J. P. McCoy, Jr., A. M. Aponte, R. F. Shen, R. S. Balaban, and T. Finkel. 2006. The mammalian target of rapamycin (mTOR) pathway regulates mitochondrial oxygen consumption and oxidative capacity. J Biol Chem 281:27643-27652.
30. Cunningham, J. T., J. T. Rodgers, D. H. Arlow, F. Vazquez, V. K. Mootha, and P. Puigserver. 2007. mTOR controls mitochondrial oxidative function through a YY1-PGC-1alpha transcriptional complex. Nature 450:736-740.
31. Peng, T., T. R. Golub, and D. M. Sabatini. 2002. The immunosuppressant rapamycin mimics a starvation-like signal distinct from amino acid and glucose deprivation. Mol Cell Biol 22:5575-5584.
32. Brown, N. F., M. Stefanovic-Racic, I. J. Sipula, and G. Perdomo. 2007. The mammalian target of rapamycin regulates lipid metabolism in primary cultures of rat hepatocytes. Metabolism 56:1500-1507.
33. Sipula, I. J., N. F. Brown, and G. Perdomo. 2006. Rapamycin-mediated inhibition of mammalian target of rapamycin in skeletal muscle cells reduces glucose utilization and increases fatty acid oxidation. Metabolism 55:1637-1644.
34. Araki, K., A. P. Turner, V. O. Shaffer, S. Gangappa, S. A. Keller, M. F. Bachmann, C. P. Larsen, and R. Ahmed. 2009. mTOR regulates memory CD8 T cell differentiation. Nature 460:108-112.
35. Zhang, Y., G. Joe, E. Hexner, J. Zhu, and S. G. Emerson. 2005. Alloreactive Memory T Cells Are Responsible for the Persistence of Graft-versus-Host Disease. J Immunol 174:3051-3058.
36. Zhang, Y., J. P. Louboutin, J. Zhu, A. J. Rivera, and S. G. Emerson. 2002. Preterminal host dendritic cells in irradiated mice prime CD8+ T cell-mediated acute graft-versus-host disease. J Clin Invest 109:1335-1344.
37. Zhang, Y., A. Harada, J. B. Wang, Y. Y. Zhang, S. Hashimoto, M. Naito, and K. Matsushima. 1998. Bifurcated dendritic cell differentiation in vitro from murine lineage phenotype-negative c-kit+ bone marrow hematopoietic progenitor cells. Blood 92:118-128.
38. Ahmed, R., A. Salmi, L. D. Butler, J. M. Chiller, and M. B. Oldstone. 1984. Selection of genetic variants of lymphocytic choriomeningitis virus in spleens of persistently infected mice. Role in suppression of cytotoxic T lymphocyte response and viral persistence. J Exp Med 160:521-540.
39. Jiang, J., L. L. Lau, and H. Shen. 2003. Selective depletion of nonspecific T cells during the early stage of immune responses to infection. J Immunol 171:4352-4358.
40. Sariban-Sohraby, S., I. T. Magrath, and R. S. Balaban. 1983. Comparison of energy metabolism in human normal and neoplastic (Burkitt's lymphoma) lymphoid cells. Cancer Res 43:4662-4664.
41. Intlekofer, A. M., N. Takemoto, E. J. Wherry, S. A. Longworth, J. T. Northrup, V. R. Palanivel, A. C. Mullen, C. R. Gasink, S. M. Kaech, J. D. Miller, L. Gapin, K. Ryan, A. P. Russ, T. Lindsten, J. S. Orange, A. W. Goldrath, R. Ahmed, and S. L. Reiner. 2005. Effector and memory CD8+ T cell fate coupled by T-bet and eomesodermin. Nat Immunol 6:1236-1244.
42. Joshi, N. S., W. Cui, A. Chandele, H. K. Lee, D. R. Urso, J. Hagman, L. Gapin, and S. M. Kaech. 2007. Inflammation directs memory precursor and short-lived effector CD8(+) T cell fates via the graded expression of T-bet transcription factor. Immunity 27:281-295.
43. Reiner, S. L. 2007. Development in motion: helper T cells at work. Cell 129:33-36.
44. Rao, R. R., Q. Li, K. Odunsi, and P. A. Shrikant. 2010. The mTOR kinase determines effector versus memory CD8+ T cell fate by regulating the expression of transcription factors T-bet and Eomesodermin. Immunity 32:67-78.
45. Jameson, S. C. 2002. Maintaining the norm: T-cell homeostasis. Nat Rev Immunol 2:547-556.
46. Sprent, J. 2003. Turnover of memory-phenotype CD8+ T cells. Microbes Infect 5:227-231.
47. Bouneaud, C., Z. Garcia, P. Kourilsky, and C. Pannetier. 2005. Lineage relationships, homeostasis, and recall capacities of central- and effector-memory CD8 T cells in vivo. J Exp Med 201:579-590.
48. Fearon, D. T., J. M. Carr, A. Telaranta, M. J. Carrasco, and J. E. Thaventhiran. 2006. The rationale for the IL-2-independent generation of the self-renewing central memory CD8+ T cells. Immunol Rev 211:104-118.
49. Kaech, S. M., and E. J. Wherry. 2007. Heterogeneity and cell-fate decisions in effector and memory CD8+ T cell differentiation during viral infection. Immunity 27:393-405.
50. Delgoffe, G. M., T. P. Kole, Y. Zheng, P. E. Zarek, K. L. Matthews, B. Xiao, P. F. Worley, S. C. Kozma, and J. D. Powell. 2009. The mTOR kinase differentially regulates effector and regulatory T cell lineage commitment. Immunity 30:832-844.
51. Wherry, E. J., S. J. Ha, S. M. Kaech, W. N. Haining, S. Sarkar, V. Kalia, S. Subramaniam, J. N. Blattman, D. L. Barber, and R. Ahmed. 2007. Molecular signature of CD8+ T cell exhaustion during chronic viral infection. Immunity 27:670-684.
52. Kim, K., C. K. Lee, T. J. Sayers, K. Muegge, and S. K. Durum. 1998. The trophic action of IL-7 on pro-T cells inhibition of apoptosis of pro-T1, -T2, and -T3 cells correlates with Bcl-2 and Bax levels and is independent of Fas and p53 pathways. J Immunol 160:5735-5741.
53. Jacobs, S. R., R. D. Michalek, and J. C. Rathmell. 2010. IL-7 is essential for homeostatic control of T cell metabolism in vivo. J Immunol 184:3461-3469.

I claim:

1. A method of generating a population of antigen-specific memory T-cells comprising:

a) processing an initial sample from a subject under conditions such that an isolated T-cell sample is generated, wherein said initial sample is selected from: a peripheral blood sample, a spleen sample, and a lymph node sample, and wherein said isolated T-cell sample comprises purified cells, wherein substantially all of said purified cells present in said T-cell sample are unprimed CD44$^-$ CD8$^+$ T-cells as a result of said processing; and b) contacting said isolated T-cell sample, which contains said unprimed CD44$^-$ CD8$^-$ T-cells, with: i) an antigen, ii) antigen presenting cells, and iii) an mTOR pathway inhibiting agent, under conditions such that a memory T-cell sample is generated that comprises memory T-cells specific to said antigen, wherein substantially all of said memory T-cells present in said memory T-cell sample are CD44⁻ CD62L⁺ CD8⁺;

wherein said mTOR pathway inhibiting agent is selected from the group consisting of: rapamycin, temsirolimus, everolimus torin, and deforolimus.

2. The method of claim 1, wherein said isolated T-cell sample is further contacted with at least one cytokine.

3. The method of claim 2, wherein said at least one cytokine comprises IL-2.

4. The method of claim 2, wherein said at least one cytokine comprises IL-21.

5. The method of claim 2, wherein said at least one cytokine is IL-2 and IL-21.

6. The method of claim 1, wherein said CD44⁻ CD62L⁺ CD8⁺ memory T cells express elevated levels, relative to cells in said initial sample, of at least one gene selected from the group consisting of: Ezh2, Hells, Bmi1, Survivin, p18$^{Ink4c}$, and p21.

7. The method of claim 1, wherein said CD44⁻ CD62L⁺ CD8⁺ memory T cells express elevated levels, relative to cells in said initial sample, of each of the following genes: Ezh2, Hells, Bmi1, Survivin, p18$^{Ink4c}$, and p21.

8. The method of claim 1, wherein said contacting further comprises contacting said isolated T-cell sample with IL-15.

9. The method of claim 1, wherein said antigen is a tumor-associated antigen.

10. The method of claim 1, wherein said mTOR pathway-inhibiting agent comprises rapamycin.

11. The method of claim 1, wherein said unprimed CD44⁻ CD8⁺ T-cells are human T-cells.

* * * * *